US007470427B2

(12) United States Patent
Cocking

(10) Patent No.: US 7,470,427 B2
(45) Date of Patent: Dec. 30, 2008

(54) SYSTEMIC NON-NODULAR ENDOSYMBIOTIC NITROGEN FIXATION IN PLANTS

(75) Inventor: Edward Charles Daniel Cocking, Nottingham (GB)

(73) Assignee: The University of Nottingham, Nottingham (GB)

( * ) Notice: Subject to any disclaimer, the term of this patent is extended or adjusted under 35 U.S.C. 154(b) by 414 days.

(21) Appl. No.: 10/488,422

(22) PCT Filed: Aug. 30, 2002

(86) PCT No.: PCT/GB02/03978

§ 371 (c)(1),
(2), (4) Date: Jun. 14, 2004

(87) PCT Pub. No.: WO03/020014

PCT Pub. Date: Mar. 13, 2003

(65) Prior Publication Data

US 2004/0235663 A1 Nov. 25, 2004

(30) Foreign Application Priority Data

Aug. 31, 2001 (GB) ................... 0121126.7

(51) Int. Cl.
*A01N 63/00* (2006.01)
*A01N 65/00* (2006.01)
*C12N 5/00* (2006.01)
*C12N 5/02* (2006.01)

(52) U.S. Cl. .............. 424/93.4; 424/93.7; 435/410; 435/822; 435/823

(58) Field of Classification Search ............... None
See application file for complete search history.

(56) References Cited

U.S. PATENT DOCUMENTS 1,909,622 A * 5/1933 Matchette ............. 435/252.2
5,664,368 A * 9/1997 Sandor ................. 47/58.1 R
6,096,528 A * 8/2000 Lu et al. ............... 435/252.1
6,670,154 B1 * 12/2003 Hitzeman et al. ....... 435/91.42

FOREIGN PATENT DOCUMENTS

EP 0 237 683 A1 9/1987
GB 2259302 * 3/1993

OTHER PUBLICATIONS

ATCC Manual, 18th ed, p. 162, 1992.*

Sevilla et al "Controb. of the bact. endophyte *Acetobacter diazotrophicus* to sugarcane nutrition: A Prel. Study", Symbiosis (1998), 25 (1-3), 181-191, see entire abstract only.*
Cocking, E.C., "The Rhizosphere and Microbial Plant Interactions", Technical Expert Meeting on Increasing the Use of Biological Nitrogen Fixation (BNF) in Agriculture. Summary Report, Mar. 13-15, 2001, pp. 1-38, FAO, Rome.*
Egener, T. et al., "Endophytic Expression of nif Genes of Azoarcus sp. Strain BH72 in Rice Roots", Molecular Plant-Microbe Interactions, 1999, pp. 813-819, vol. 12, No. 9, The American Phytopathological Society.*
Fuentes-Ramirez, L.E. et al., "Colonization of Surgarcane by Acetobacter Diazotrophicus is Inhibited by High N-Fertilization", FEMS Microbiology Ecology, Jun. 1999, pp. 117-128, vol. 29, No. 2, Elsevier Science B.V.*
Gantar, M., "Co-Cultivation of N2-Fixing Cyanobacterium Nostoc sp. Strain 2S9B and Wheat Callus", Symbiosis, 2000, pp. 1-18, vol. 29, No. 1, Balaban, Rehovot, IL, USA.*
Gantar, M., "Mechanical Damage of Roots Provides Enhanced Colonization of the Wheat Endorizosphere by the Dinitrogen-Fixing Cyanbacterium Nostoc sp. Strain 2S9B", Biology and Fertility of Soils, 2000, pp. 250-255, vol. 32, No. 3, Springer-Verlag 2000.*
James, E.K., "Nitrogen Fixation in Endophytic and Associative Symbiosis", Field Crops Research, 2000, pp. 197-209, vol. 65, Elsevier Science B.V.*
Mylona, P. et al., "Symbiotic Nitrogen Fixation", The Plant Cell, Jul. 1995, pp. 869-885, vol., No. 7.*
Rai, A.N. et al., "Cyanobacterium-Plant Symbioses", New Phytologist, Sep. 2000, pp. 449-481, vol. 147, No. 3.*
Sevilla, M. et al., "Comparison of Benefit to Surgence Plant Growth and 15N2 Incorporation Following Inoculation of Sterile Plants with Acetobacter Diazotrophicus Wild-Type and Nif Mutant Strains", Molecular Plant-Microbe Interactions, 2001, pp. 358-366, vol. 14, No. 3, The American Phytopathological Society.*
Sevilla, M. et al., "Contributions of the Bacterial Endophyte Acebacter Diazotrophicus to Sugarcane Nutrition: A Preliminary Study", Symbiosis, 1998, pp. 181-191, vol. 25, Balaban, Rehovot, IL., USA.*

* cited by examiner

*Primary Examiner*—David M. Naff
*Assistant Examiner*—Deborah K. Ware
(74) *Attorney, Agent, or Firm*—Mathews, Shepherd, McKay & Bruneau, P.A.

(57) ABSTRACT

Non-leguminous crops, e.g. wheat, maize and rice, do not form nodules and are dependant for their nutrition on fixed nitrogen from the soil, or from chemical/nitrogenous fertilizers. The present invention provides non-leguminous plants and leguminous plants, including legumes that fail to nodulate with *Rhizobia*, with bacteria that enable them to fix nitrogen endophytically. Therefore, the plants contain nitrogen fixing bacteria the bacteria being located intacellularly in living plant cells.

9 Claims, 22 Drawing Sheets

SYSTEMIC NON-NODULAR ENDOSYMBIOTIC NITROGEN FIXATION IN PLANTS

This invention relates to nitrogen fixation and in particular, but not exclusively, to nitrogen fixation in non-leguminous and leguminous plants, to a method of establishing nitrogen fixation in non-leguminous and leguminous plants and to a plant, without nodules, obtained by way of such a method.

Although nitrogen gas ($N_2$) makes up 78% of the atmosphere, it is unavailable for use by plants and most other organisms because there is a triple bond between the two nitrogen atoms, making the molecule almost inert. In order for nitrogen gas to be used for growth it must first be fixed (i.e., reduced by hydrogen to ammonia) and be available in the combined form of ammonium ($NH_4^+$) or nitrate ($NO_3^-$); certain types of bacteria can carry out this biological nitrogen fixation by reducing gaseous nitrogen to ammonia ($NH_3$) enzymatically utilizing the enzyme nitrogenase. The availability of fixed nitrogen is often the limiting factor for plant growth and biomass production in environments where there is a suitable climate and availability of water to support life.

Chemically most ammonia is produced industrially by the Haber-Bosch process by catalytically combining atmospheric nitrogen with hydrogen to form ammonia, using an iron-based catalyst at high temperature and very high pressure. A relatively very small amount of ammonia is produced as a result of lightning discharges in the atmosphere.

The demand for increased crop yields in the 20th Century and into this Century has required biological nitrogen fixation by bacteria to be supplemented increasingly by the use of fixed nitrogen from chemical fertilisers.

Biological nitrogen fixation can be represented by the following equation, in which two molecules of ammonia are produced from one molecule of nitrogen gas, at the expense of 16 molecules of adenosine triphosphate (ATP) and a supply of electrons and protons (hydrogen ions):—

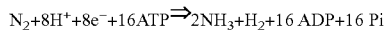

$$N_2 + 8H^+ + 8e^- + 16 ATP \Rightarrow 2NH_3 + H_2 + 16 ADP + 16 Pi$$

This reaction is performed in bacteria, using an enzyme complex called nitrogenase. This enzyme consists of two proteins—an iron (Fe) protein and a Molybdenum-Iron (Mo—Fe) protein.

The reaction occurs while $N_2$ is bound to the nitrogenase enzyme complex. The Fe protein is first reduced by electrons donated by ferredoxin. The reduced Fe—protein then binds ATP and reduces the Mo—Fe protein, which donates electrons to $N_2$, producing HN═NH. In two further cycles of this process (each requiring electrons donated by ferredoxin) HN═NH is reduced to $H_2N$—$NH_2$ and this in turn is reduced to $2NH_3$.

Depending on the type of bacteria, the reduced ferredoxin which supplies electrons for this process is generated by photosynthesis, respiration or fermentation.

The most familiar examples of nitrogen fixing symbioses between plants and rhizobial bacteria are the root nodules of legumes (peas, beans, clover and the like). In these symbioses the rhizobia "invade" the plant via root hairs or crack entry sites (i.e. intercellularly between epidermal cells) and cause the formation of a nodule by inducing localised proliferation of the plant host cells. Subsequently, the rhizobia invade the cells of the nodule by penetrating the cell wall and being engulfed by invaginations from the plasma membrane (endocytosis). Consequently within the cells of the nodule the rhizobia are enclosed in membrane bounded vesicles (small vacuoles) in which they fix nitrogen, utilising products of plant photosynthesis as carbon and energy sources, and supply biologically fixed nitrogen to the plant for growth and development (endosymbiosis). The bacterial microsymbiont is intracellular, but is always extra-cytoplasmic because of the integrity of the surrounding membrane.

Non-legume crops, which include the main cereals of the world e.g. wheat, maize and rice, do not form nodules and are dependent on fixed nitrogen from the soil for their nutrition, or from chemical/nitrogenous fertilisers.

However, energy and environmental concerns arising from the overuse of nitrogenous fertilisers have highlighted a need for non-leguminous crops to obtain more of their nitrogen from the air by biological nitrogen fixation.

It is known that an intercellular, systemic, endophytic nitrogen fixing interaction with *Acetobacter diazotrophicus* and *Herbaspirillum* spp., without the need for nodulation, occurs naturally in Brazilian varieties of sugar cane. Sugar cane is a member of the grass family, Gramineae, which also includes cereals. This non-nodular, intercellular, endophytic nitrogen fixing relationship may also be possible in rice, wheat, maize and in other non-legume crops.

From several published, peer reviewed, academic papers in the art it is also known that there is no evidence that endophytic nitrogen fixation between diazotrophic bacteria and the host plant occurs intracellularly in living cells. For example, from Biological Nitrogen fixation for the 21st Century pp 685-692 states that there is no evidence for the presence of endophytic diazotrophic bacteria within living cells. James in "Field Crops Research 2000 pp 197-209" describes that "endophytic diazotrophs have been observed only within intercellular spaces, vascular tissue, aerenchyma and dead cells of their hosts and not in living cells". Egener et al., in "MPMI Vol. 12 (1999) pp 813-819" also describe that there is no evidence for endophytic diazotrophic bacteria inside living cells of plants.

The present invention aims to provide non-leguminous plants and leguminous plants, including legumes that fail to nodulate with rhizobia, with bacteria that enable them to fix nitrogen endophytically, therefore addressing many of the problems associated with the use of chemical/nitrogenous fertilisers.

Accordingly, the present invention, in a first aspect, provides a non-leguminous or leguminous plant containing nitrogen fixing bacteria, said bacteria being located intracellularly in living plant cells providing fixed nitrogen to said plant.

According to the second aspect, the present invention further provides a method of inoculating a non-leguminous or a leguminous plant with nitrogen fixing bacteria, said bacteria being located intracellularly in living plant cells and providing fixed nitrogen to said plant.

The non-leguminous plant is preferably selected from the grass family Gramineae (includes rice [*Oryza sativa*], wheat [*Triticum aestivum*] and maize [*Zea mays*]). The non-leguminous plant may also be one selected from families such as: Solanaceae (includes tomato, potato and tobacco), Brassicaceae/Cruciferae (includes cabbages, turnips, oilseed rape and the model plant *Arabidopsis thaliana*), Malvaceae (includes cotton), Compositae/Asteraceae (includes sunflower and lettuce), Euphorbiaceae (includes cassava), Chenopodiaceae (includes sugar beet). The leguminous plant is preferably selected from the Leguminosae (includes soybean, clover, alfalfa, peas and other beans).

The non-leguminous plant, or leguminous plant, may be inoculated with between 1 to $1 \times 10^7$ bacteria per milliliter of inoculum. The non-leguminous plant or leguminous plant is preferably inoculated with between 1 to 100 bacteria per milliliter of inoculum.

The non-leguminous plant, or leguminous plant, is more preferably inoculated with 1-10 bacteria per millilitre of inoculum. The non-leguminous, or leguminous, plant is most preferably inoculated with 1-2 bacteria per millilitre of inoculum. IdeallyThe non leguminous, or leguminous, plant is most preferably inoculated with one bacterium per millilitre of inoculum.

The non-leguminous, or leguminous, plant is preferably inoculated when germination occurs or up to about seven days thereafter.

The nitrogen fixing bacterium used to inoculate the non-leguminous, or leguminous, plant is preferably *Acetobacter diazotrophicus* (syn. *Gluconacetobacter diazotrophicus*). Alternatively the nitrogen fixing bacterium used for inoculation may be a species of *Herbaspirillum*.

We have found that using a very low concentration of bacteria in the inoculum we can obtain plants that are healthier that those inoculated with higher concentrations of bacteria. We have also found that *Acetobacter diazotrophicus* secretes large amounts of indole acetic acid (IAA), a plant growth hormone. It is known that the response of various plant species to external (microbially released) IAA can vary from beneficial to deleterious effects, depending on the concentration of IAA in the plant root. In general, when IAA is present in higher concentrations than would normally be found in a plant, the increased concentration of IAA inhibits growth, and alters the phenotype of the plant. Also, at low concentrations IAA (or other plant growth substances) secreted by bacteria may be acting as a plant-bacterial (and other plant growth substances) signalling molecule for the intracellular endophytic establishment of *Acetobacter diazotrophicus*.

The nitrogen fixing bacteria may fix nitrogen in the presence of up to 10% oxygen. Preferably the bacteria fix nitrogen in the presence of between 2% to 7% oxygen.

The nitrogen fixing bacteria are intracellular. The intracellular nitrogen fixing bacteria are more preferably present in membrane bounded vesicles and vacuoles within the cytoplasm of the plant cell.

The nitrogen fixing bacteria are preferably found in colonies in vesicles and vacuoles.

The colonies are preferably located in structures that are polyhedral in configuration. Most preferably the structures are substantially rhomboidal in shape.

These structures are capsules of levan, an oligo fructoside polymer of β-D-fructose secreted by *A. diazotrophicus*.

It is a surprising and unexpected result that the present invention provides a systemic, non-nodular, intracellular symbiosis between the nitrogen fixing bacteria and a non-leguminous plant, said bacteria being located within the living cells of the plant. This has not been observed before. As mentioned previously, it is known that in other symbioses between nitrogen fixing bacteria and other non-leguminous plants, e.g., sugar cane, the bacteria exist in the intercellular spaces between cells (the apoplast) and within the dead cells of the xylem.

It is also a surprising and unexpected result that the present invention provides a similar systemic, non-nodular intracellular symbiosis between nitrogen fixing bacteria and a leguminous, or non-leguminous plant, said bacteria being located within the living cells of the plant. This has not been observed before.

Another surprising and unexpected result is that the nitrogen fixing bacteria, are located intracellularly in living cells within vesicles and vacuoles in the cytoplasm in both a non-leguminous plant and a leguminous plant.

The bacteria may spread from plant cell to plant cell by division of plant cells in the meristem and subsequent divisions thereof.

The bacteria may become systemic by moving through the xylem. Alternatively they may become systemic by division of plant cells and subsequent divisions thereof. The bacteria may become systemic by combinations of the above.

Accordingly, the present invention further provides, in a third aspect, a method of producing a leguminous or non-leguminous plant containing nitrogen fixing bacteria said bacteria being located intracellularly in living plant cells, wherein said bacteria have been introduced by inoculation and have become systemic by division of plant cells and subsequent divisions thereof.

According to a fourth aspect, the present invention still further provides a leguminous or non-leguminous plant containing nitrogen fixing bacteria said bacteria being located intracellularly in living plant cells, said bacteria becoming systemic in the plant by division of plant cells and subsequent divisions thereof.

Preferably the nitrogen fixing bacteria are introduced into the plant by inoculation.

Preferably the bacteria of systemically colonized plants may be propagated vegetatively to successive generations of non-leguminous plants or leguminous plants by vegetative propagation or by sexual propagation of the plant.

Accordingly the present invention, in a fifth aspect, further provides a method of producing a leguminous or non-leguminous plant containing nitrogen fixing bacteria said bacteria being located intracellularly in living plant cells said method comprising propagating a first plant containing nitrogen fixing bacteria to provide successive generations of said plant containing nitrogen fixing bacteria.

Preferably the nitrogen fixing bacteria are introduced into the first plant by inoculation.

According to a sixth aspect, the present invention provides a plant containing nitrogen fixing bacteria said bacteria being located intracellularly in living plant cells, said plant, and concomitantly, said bacteria having been vegetatively propagated or sexually propagated. Said plant is preferably propagated from a first plant inoculated with nitrogen fixing bacteria or from progations of said first plant.

According to a seventh aspect the present invention provides seeds obtainable from a plant having nitrogen fixing bacteria according to the present invention, said seed being such that upon germination of the seed said bacteria are located intracellularly in living cells, and provide fixed nitrogen to said plant.

According to an eighth aspect the present invention provides a seed of a leguminous or non leguminous plant, said seed having a coat comprising nitrogen fixing bacteria in an effective amount such that upon germination said effective amount of bacteria enter the plant and are located intracellularly within living cells said bacteria providing fixed nitrogen to said plant.

The seed coating will be one selected from seed coatings that are known in the art.

The nitrogen fixing bacteria provided in the seed coat is preferably *Acetobacter diazotrophicus* (syn. *Gluconacetobacter diazotrophicus*). Alternatively the nitrogen fixing bacterium is a species of *Herbaspirillum*.

The effective amount of bacteria is between 1 to $1 \times 10^7$ bacteria per millilitre of seed coating. The effective amount of bacteria is preferably between 1 to $1 \times 10^5$ bacteria per millilitre of seed coating. Most preferably the effective amount of bacteria is between 1 to $1 \times 10^3$ bacteria per millilitre of seed coating.

According to a ninth aspect the present invention provides a seed of a leguminous or non-leguminous plant, said seed being located in a substrate, said substrate having nitrogen fixing bacteria in an effective amount such that upon germination said effective amount of bacteria enter the plant and are located intracellularly within living cells, said bacteria providing fixed nitrogen to said plant.

The substrate is preferably a soil. However it will be appreciated that various substrates for germinating seeds are known and a suitable substrate may be selected from those that are well known in the art.

The nitrogen fixing bacteria provided in the substrate is preferably *Acetobacter diazotrophicus* (syn *Gluconacetobacter diazotrophicus*). Alternatively the nitrogen fixing bacterium is a species of *Herbaspirillum*.

The effective amount of bacteria is between 1 to $1\times10^7$ bacteria per gram of substratePreferably, the effective amount of bacteria is between 1 to $1\times10^5$ per gram of substrate. Most preferably the effective amount of bacteria is between 1 to $1\times10^3$ per gram of substrate.

The present invention will now be described, merely by way of example, with reference to the accompanying Figures, of which:—

FIGS. 1 to 13 relate to the present invention in a non-leguminous plant *Lycopersicon esculentum*; tomato).

FIGS. 1A and B shows *A. diazotrophicus* UAP 5541/pRGS561 GUS invading the meristem and root hairs (A) and meristem cells (B) of lateral roots of an inoculated plant in accordance with the present invention. Bar=25 µm (A) and 5 µm (B)

FIGS. 1C and D shows *A. diazotrophicus* UAP 5541/pRGS561 GUS in vesicles and vacuoles in thin sections of cells of the meristem of an inoculated plant in accordance with the present invention. Bar=5 µm (C and D)

FIG. 2A shows *A. diazotrophicus* UAP5541/pRGS561 GUS colonies in the xylem of lateral roots in an inoculated plant in accordance with the present invention. Bar=5 µm FIG. 2B show *A. diazotrophicus* UAP5541/pRGS561 GUS in cells of the cortex near to invaded xylem in an inoculated plant in accordance with the present invention. Bar=5 µm.

Figure 4A:
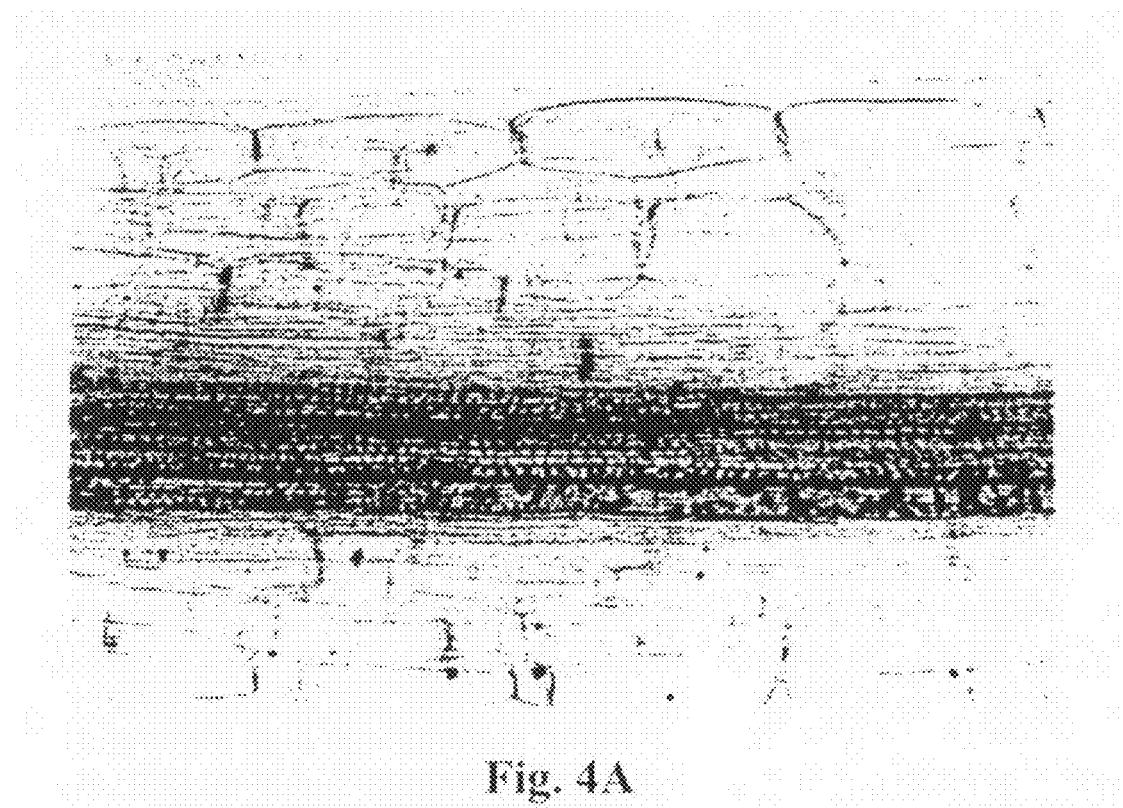

FIGS. 4A and B show *A. diazotrophicus* UAP 5541/pRGS561 GUS colonisation of the cortex and the xylem in the root of a plant according to the present invention. Bar=25 µm (A and B).

Figure 4B:
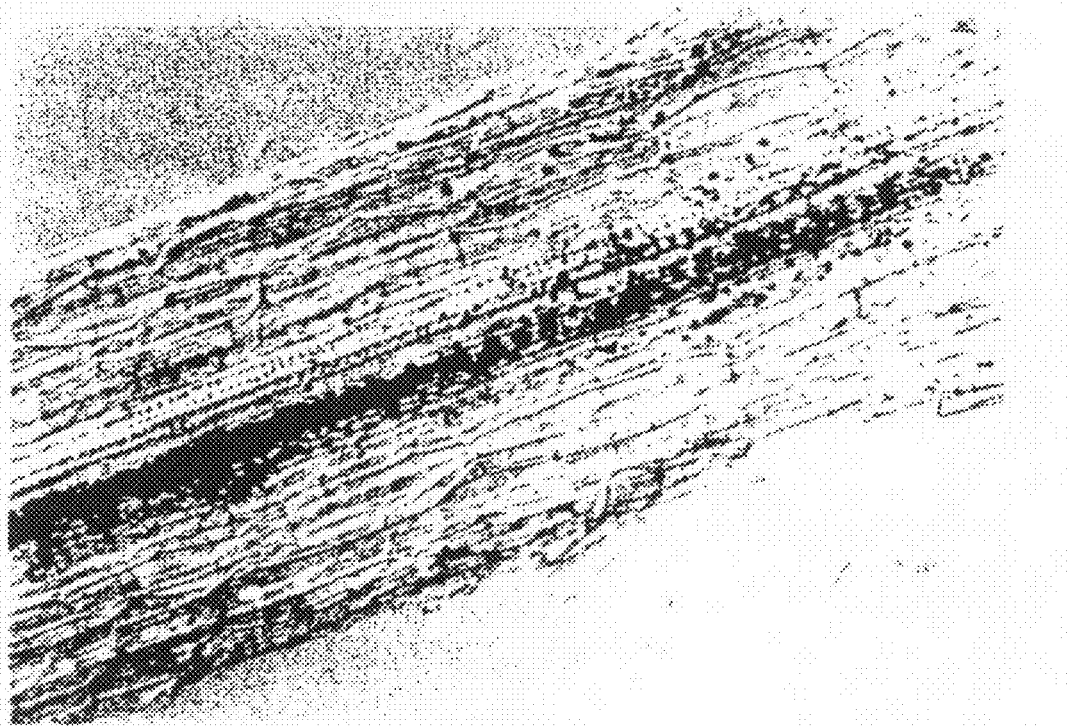
Figure 4C:
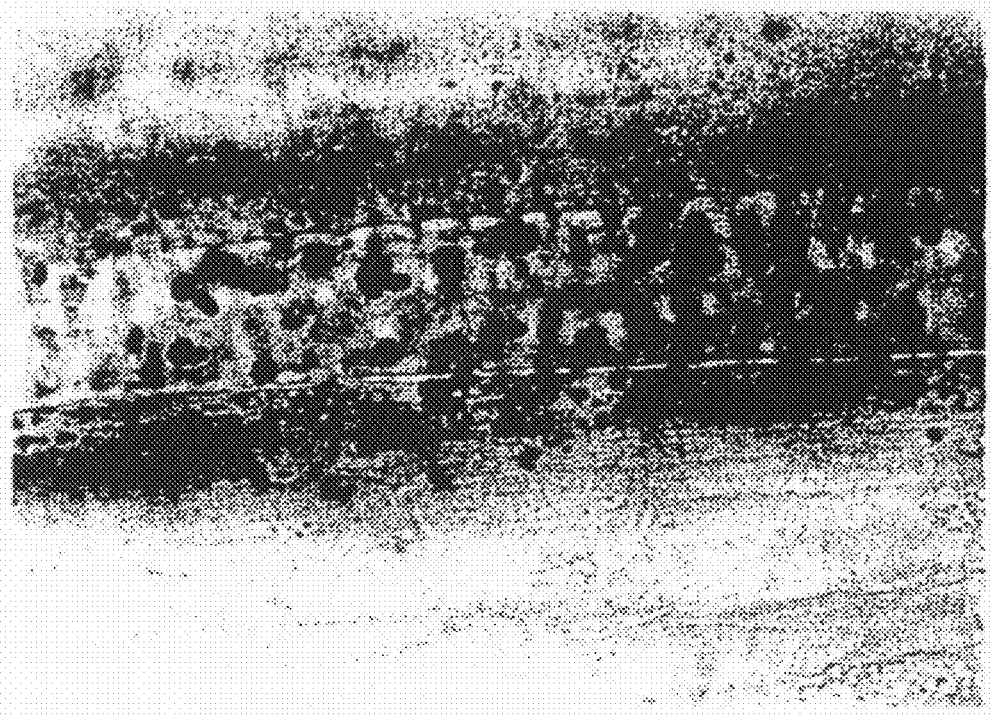

FIG. 4C shows *A. diazotrophicus* UAP5541/pRGS561 GUS colonisation from the xylem to the phloem and cortex cells of a root of a plant in accordance with the present invention. Bar=5 µm.

Figure 4D:
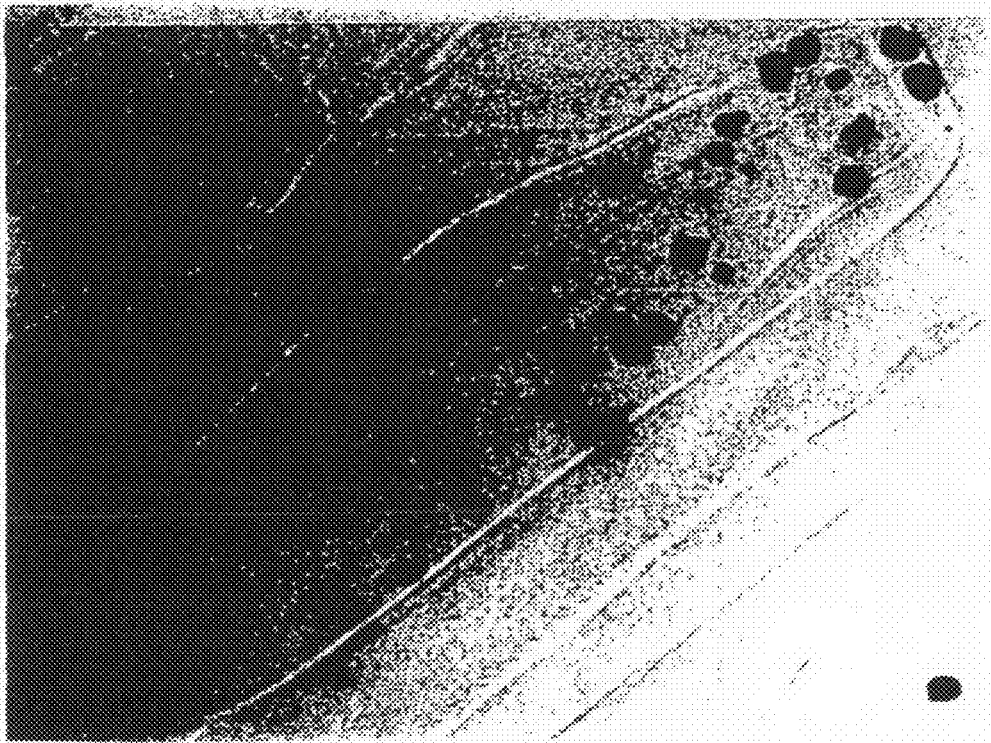

FIG. 4D shows colonies of *A. diazotrophicus* UAP5541/pRGS561 GUS inside a cortex cell of a root from a plant according to the present invention. Bar=5 µm.

Figure 5:
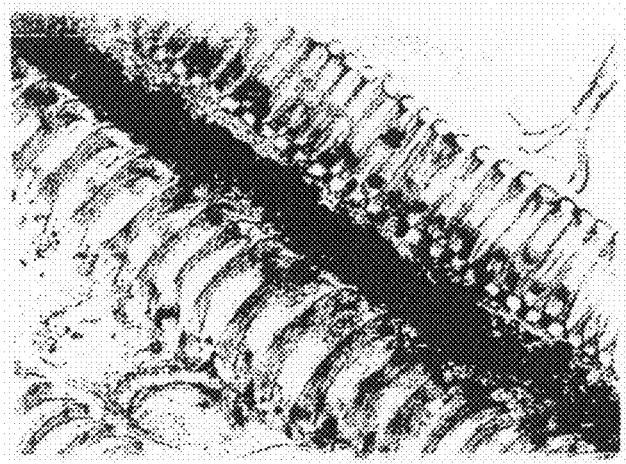

FIG. 5 shows *A. diazotrophicus* UAP5541/pRGS561 GUS colonisation spreading from the xylem to the phloem in the stem of a plant according to the present invention. Bar=5 µm.

Figure 6:
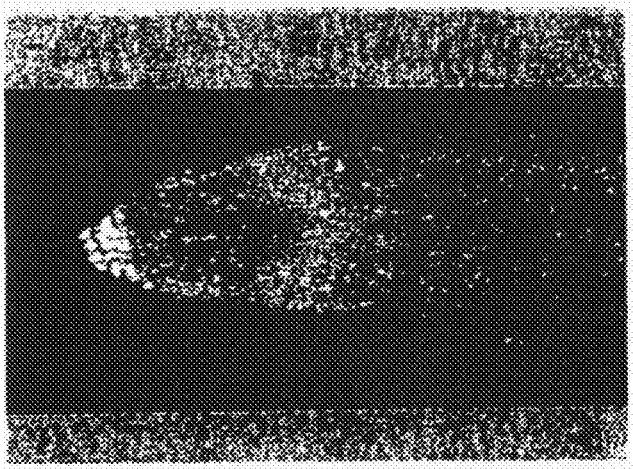

FIG. 6 shows *A. diazotrophicus* UAP 5541/pRGH562 (NifH-GUSA) in the root tip of a plant according to the present invention. (dark field illumination) Bar=50 µm.

Figure 7:
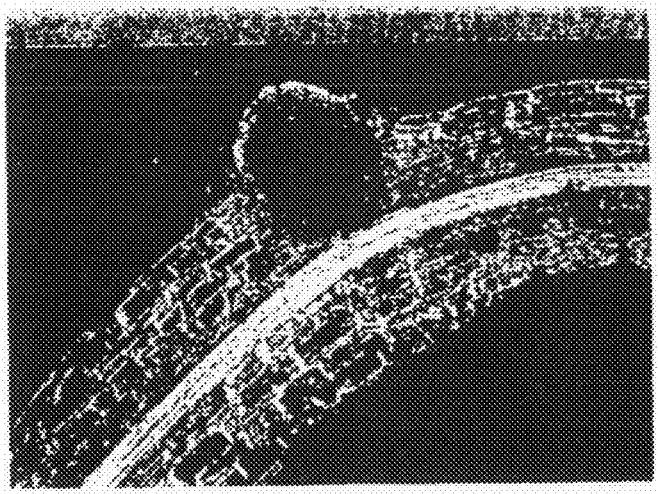

FIG. 7 shows *A. diazotrophicus* UAP 5541/pRGH562 (NifH-GUSA) colonising an emerging secondary lateral root of a plant according to the present invention. (dark field illumination) Bar=50 µm.

Figure 8A:

FIG. 8A shows colonies of *A. diazotrophicus* UAP 5541/pRGH562 (NifH-GUSA) in the meristem of a root of a plant in accordance with the present invention. Bar=25 µm.

Figure 8B:
Figure 9:

FIG. 8B shows colonies of *A. diazotrophicus* UAP5541/pRGH562 (NifH-GUSA) in cells of the root meristem of a plant in accordance with the present invention. Bar=5 µm FIG. 9 shows uniformly crystalline-like rhomboidal colonies of *A. diazotrophicus* UAP5541/pRGH562 (NifH-GUSA) in cells of the root cortex in a plant according to the present invention. Bar=5 µm.

Figure 10:
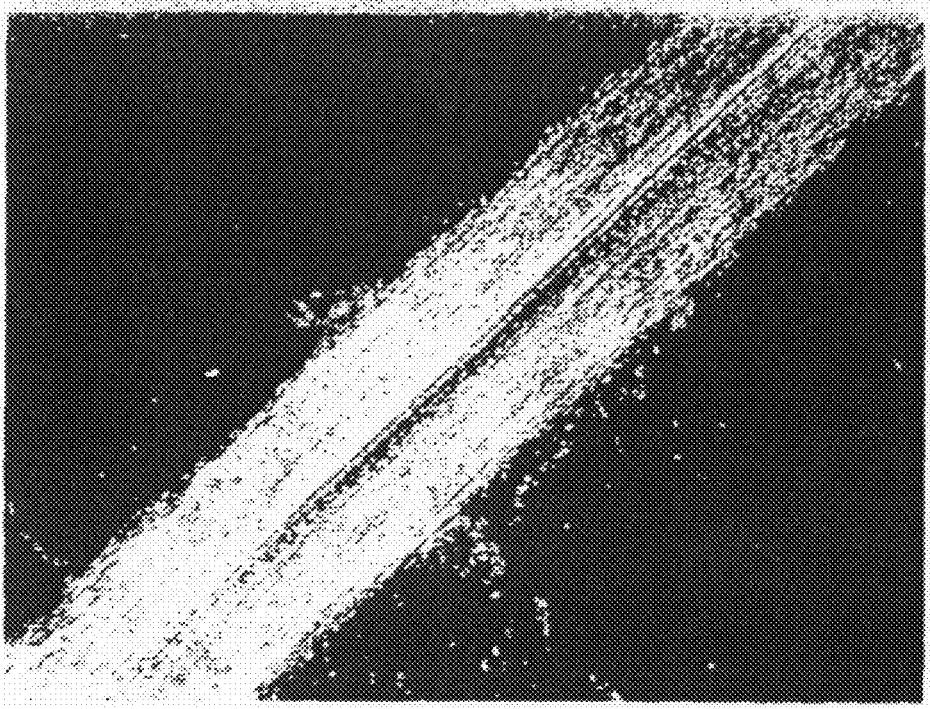

FIG. 10 shows colonies of *A. diazotrophicus* UAP 5541/pRGH562 (NifH-GUSA) in the vascular system of the root of a plant according to the present invention. (Dark field illumination) Bar=50 µm.

Figure 11:
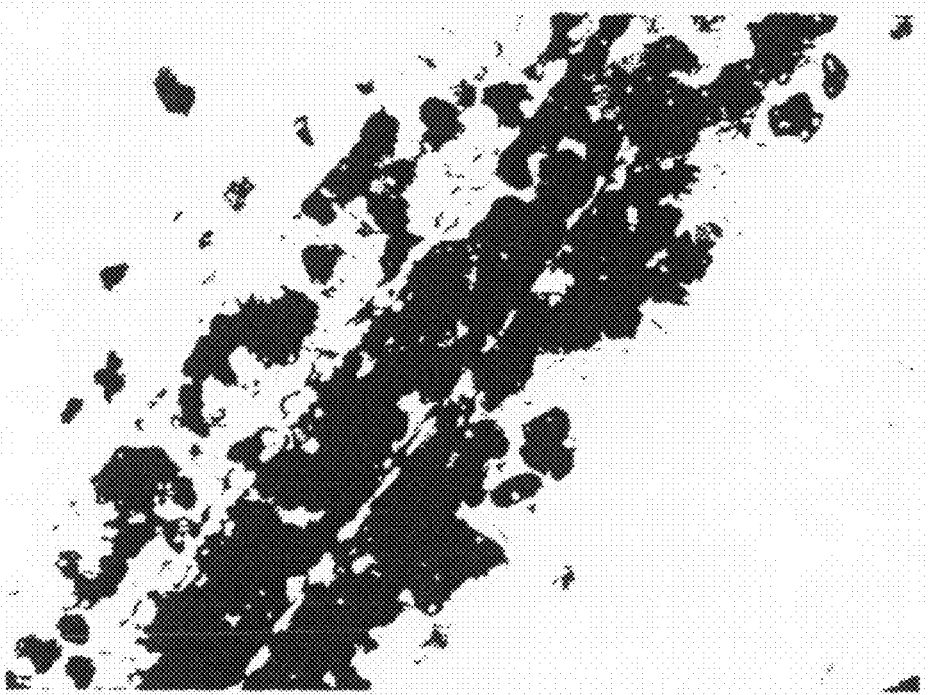

FIG. 11 shows colonies of *A. diazotrophicus* UAP5541/pRGH562 (NifH-GUSA) in the xylem and cortex of the root of a plant according to the present invention. Bar=5 µm.

Figure 12:
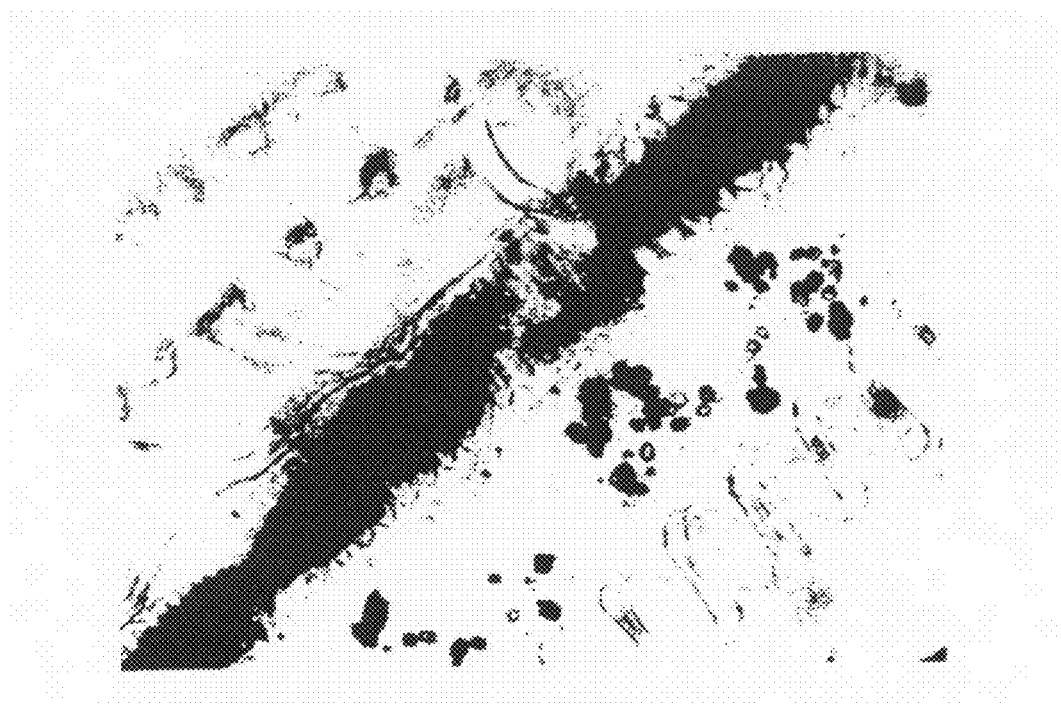

FIG. 12 shows the spread of *A. diazotrophicus* UAP 5541/pRGH562 (NifH-GUSA) from the xylem to the phloem region in the stem of a plant according to the present invention. Bar=5 µm.

Figure 13:
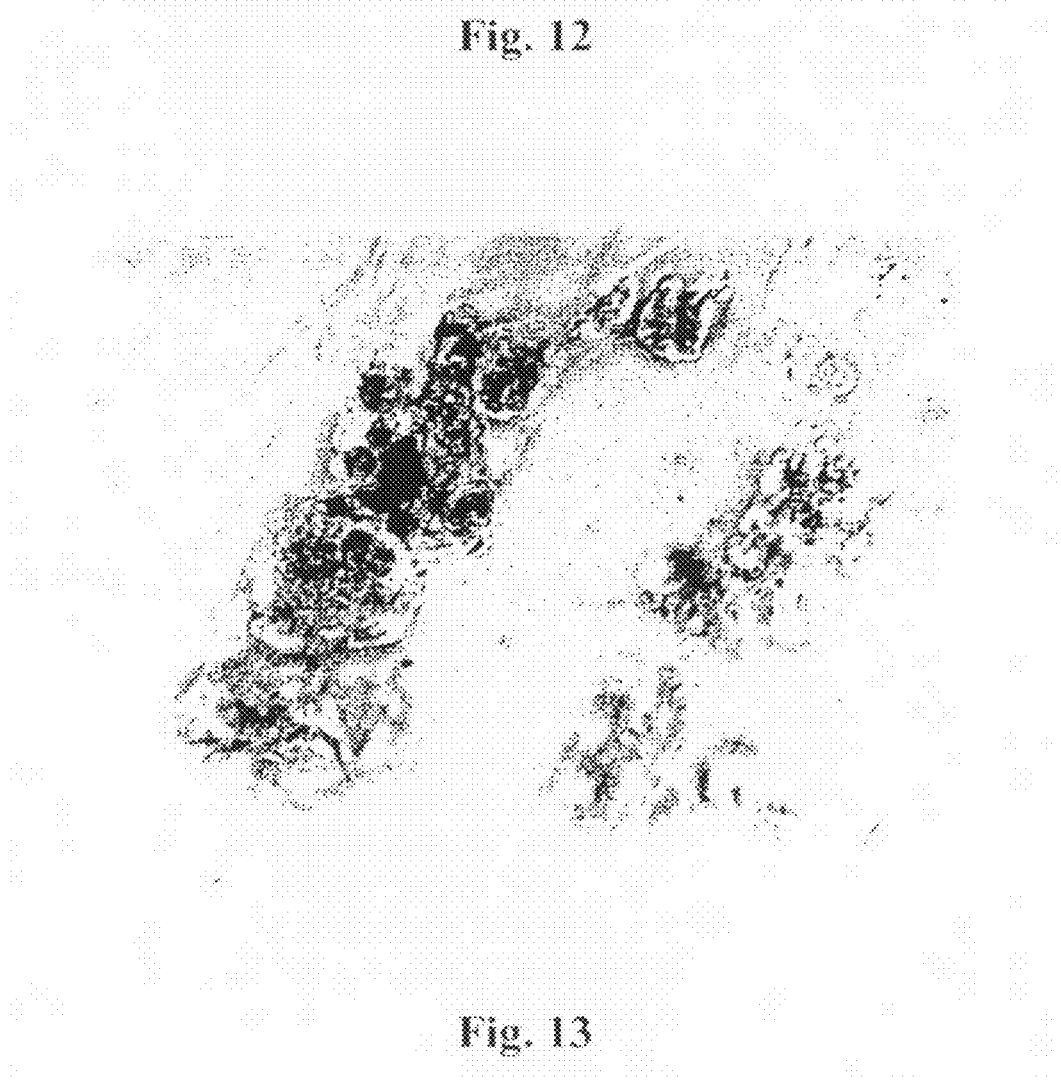

FIG. 13 shows *A. diazotrophicus* UAP 5541/pRGH562 (NifH-GUSA) in chloroplast containing cells in the stem of a plant according to the present invention. Bar=5 µm FIGS. 14 to 19 relate to the present invention in a leguminous plant (*Trifolium repens*, white clover).

Figure 14:
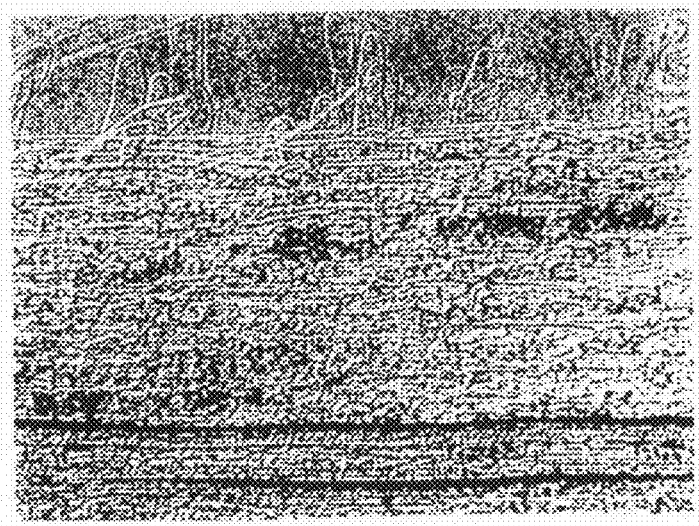

FIG. 14 shows *A. diazotrophicus* UAP 5541/pRGH562 (NifH-GUSA) in the vascular system and in cells of the cortex of the root of a plant according to the present invention. Bar=25 µm.

Figure 15:
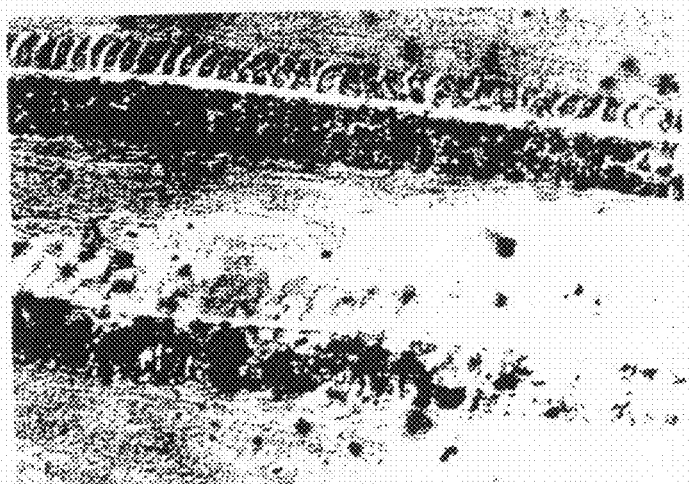

FIG. 15 shows *A. diazotrophicus* UAP 5541/pRGH562 (NifH-GUSA) in the xylem and phloem region of the root of a plant according to the present invention. Bar=5 µm.

Figure 16:
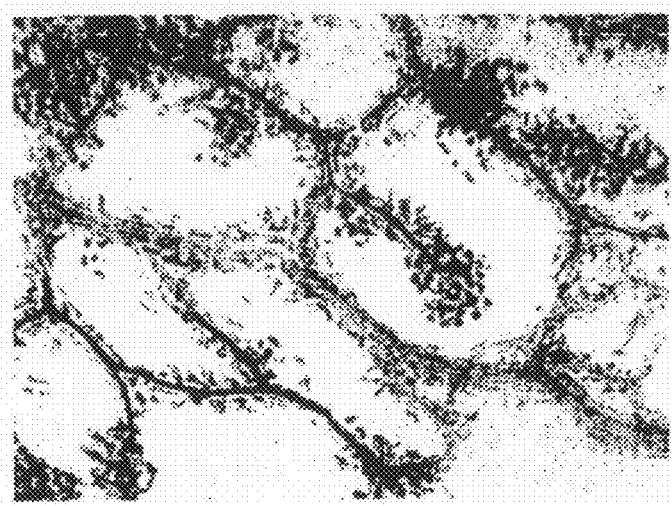

FIG. 16 shows *A. diazotrophicus* UAP 5541/pRGH562 (NifH-GUSA) in the vascular system of the leaf of a plant according to the present invention. Bar=50 µm.

Figure 17:
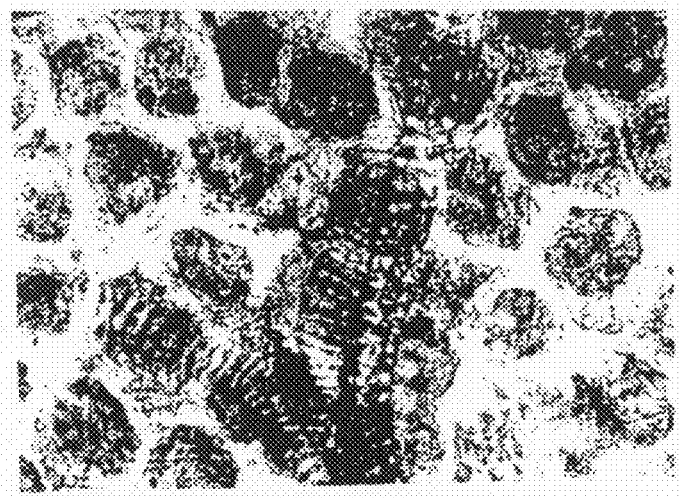

FIG. 17 shows *A. diazotrophicus* UAP 5541/pRGH562 (NifH-GUSA) in the xylem of a leaf vein of a plant according to the present invention. Bar=5 µm.

Figure 18:

FIG. 18 shows spread of *A. diazotrophicus* UAP 5541/pRGH562 (NifH-GUSA) from the xylem to mesophyll (chloroplast containing cells) of the leaf of a plant according to the present invention. Bar=25 µm.

Figure 19:
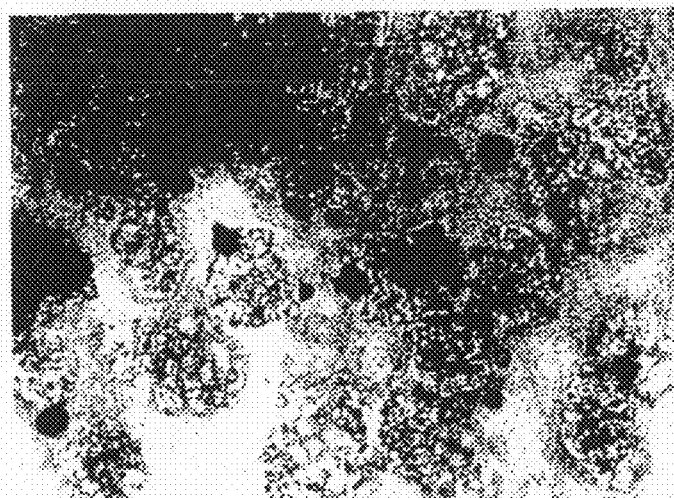

FIG. 19 shows *A. diazotrophicus* UAP 5541/pRGH562 (NifH-GUSA) in chloroplast containing mesophyll cells of a leaf of a plant according to the present invention. Bar=5 µm.

Figure 20:
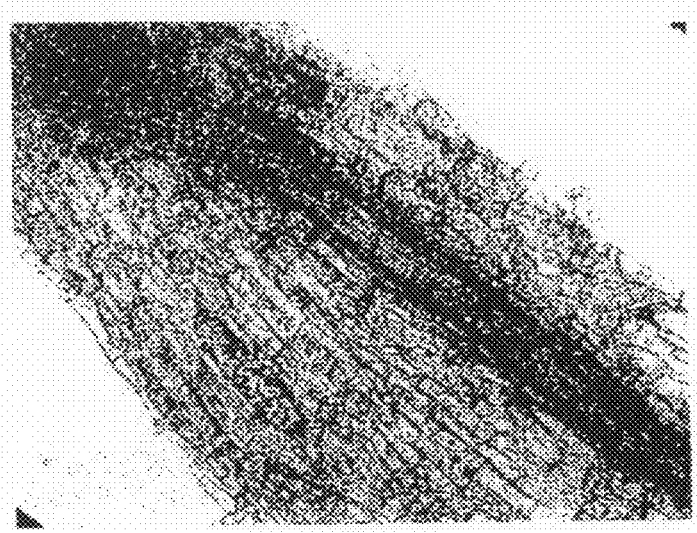
Figure 21:
Figure 22:
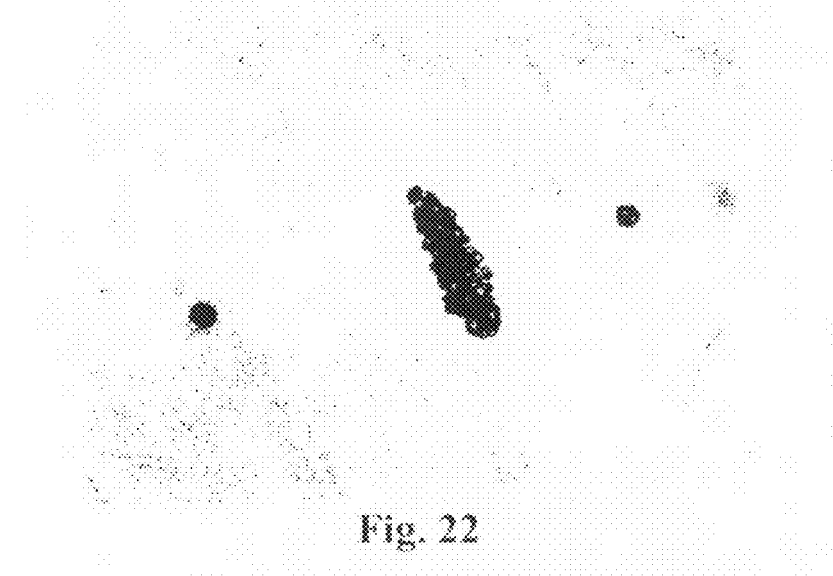

FIGS. 20 to 22 relate to the present invention in the cereal wheat (*Triticum aestivum*)

FIG. 20 shows *A. diazotrophicus* UAP5541/pRGH562 (NifH-GUSA) invading cells of the young root cortex of a lateral root of an inoculated plant in accordance with the present invention. Bar=25 µm FIG. 21 shows at high magnification colonies of *A. diazotrophicus*, as in FIG. 20, in a cortical cell of the lateral root. Bar=5 µm FIG. 22 shows a cluster of colonies of *A. diazotrophicus* UAP5541/pRGH562 (NifH-GUSA) in the vacuole of a leaf epidermal cell, after treatment with ethanol to remove chlorophyll from the leaf. Bar=5 µm FIGS. 23 to 25 relate to the present invention in oilseed rape (*Brassica napus*)

Figure 23:
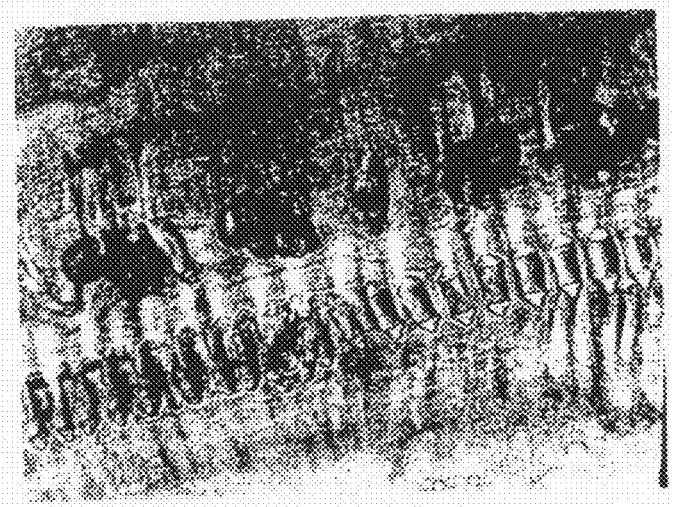
Figure 24:
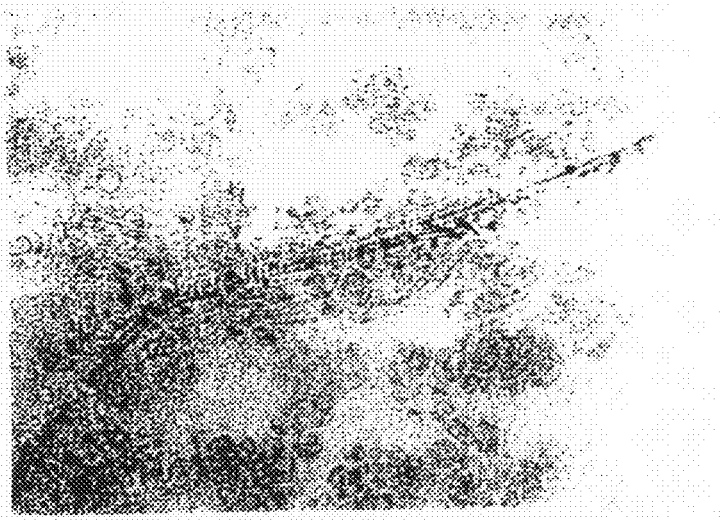
Figure 25:
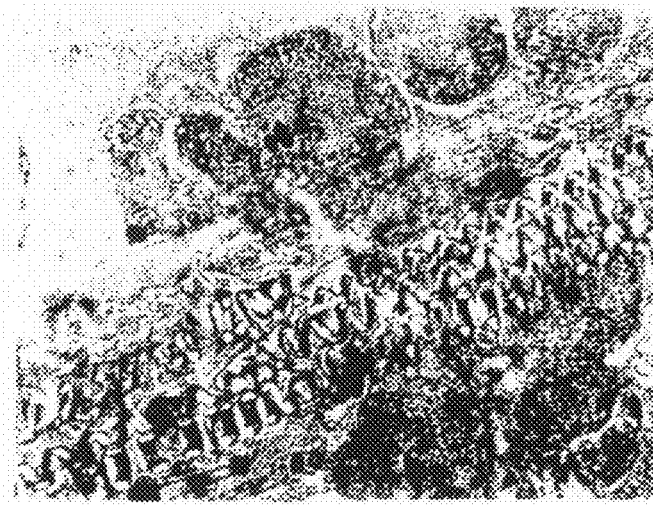

FIG. 23 shows *A. diazotrophicus* UAP5541/pRGH562 (NifH-GUSA) in the xylem of the stem of an inoculated plant in accordance with the present invention. Bar=5 µm FIG. 24 shows *A. diazotrophicus* UAP5541/pRGH562 (NifH-GUSA) in the xylem of the stem of an inoculated plant in accordance with the present invention. Bar=25 µm FIG. 25 shows *A. diazotrophicus* UAP5541/pRGH562 (NifH-GUSA) in chloroplast containing cells of the stem of an inoculated plant in accordance with the present invention. Bar=5 µm FIGS. 26 and 27 relate to the present invention in the cereal rice (*Oryza sativa*)

Figure 26:
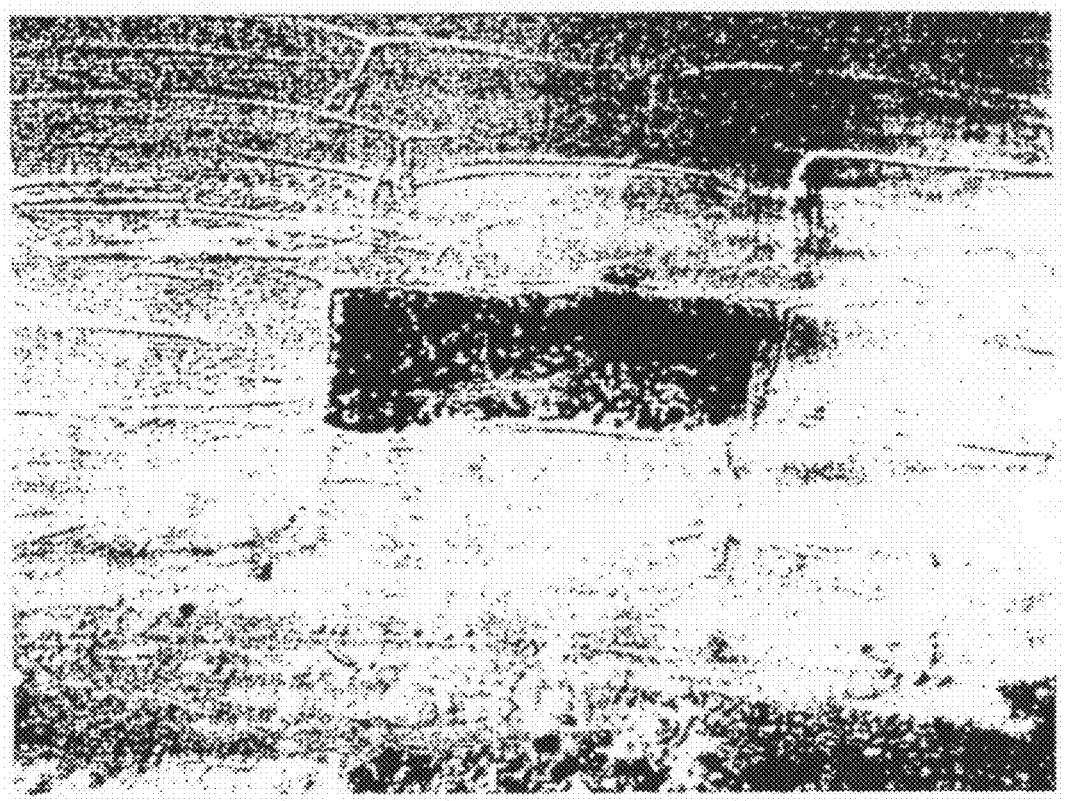
Figure 27:
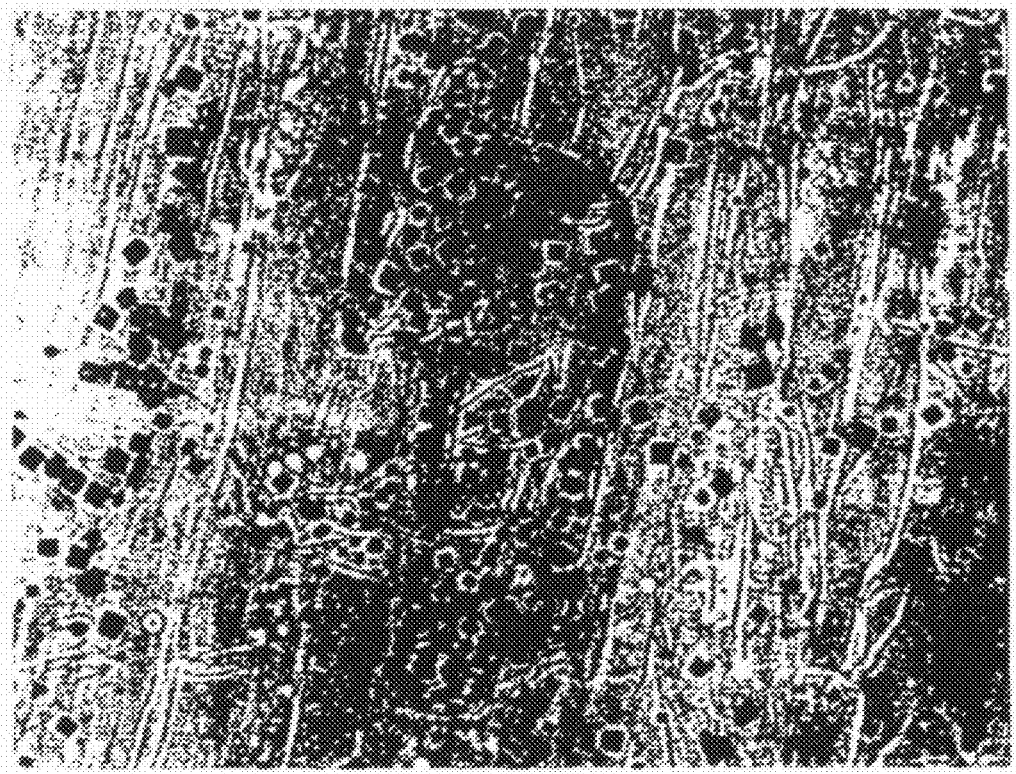

FIG. 26 shows *A. diazotrophicus* UAP5541/pRGH562 (NifH-GUSA) invading a cell of the root cortex of rice several cells below the epidermis of the young root of an inoculated plant in accordance with the present invention. Bar=5 µm FIG. 27 shows *A. diazotrophicus* UAP5541/pRGH562 (NifH-GUSA) invading cells of the cortex of a mature rice root of an inoculated plant in accordance with the present invention. Bar=5 µm FIGS. 28 and 29 relate to the present invention in the non-legume Arabidopsis (*Arabidopsis thaliana*).

Figure 28:
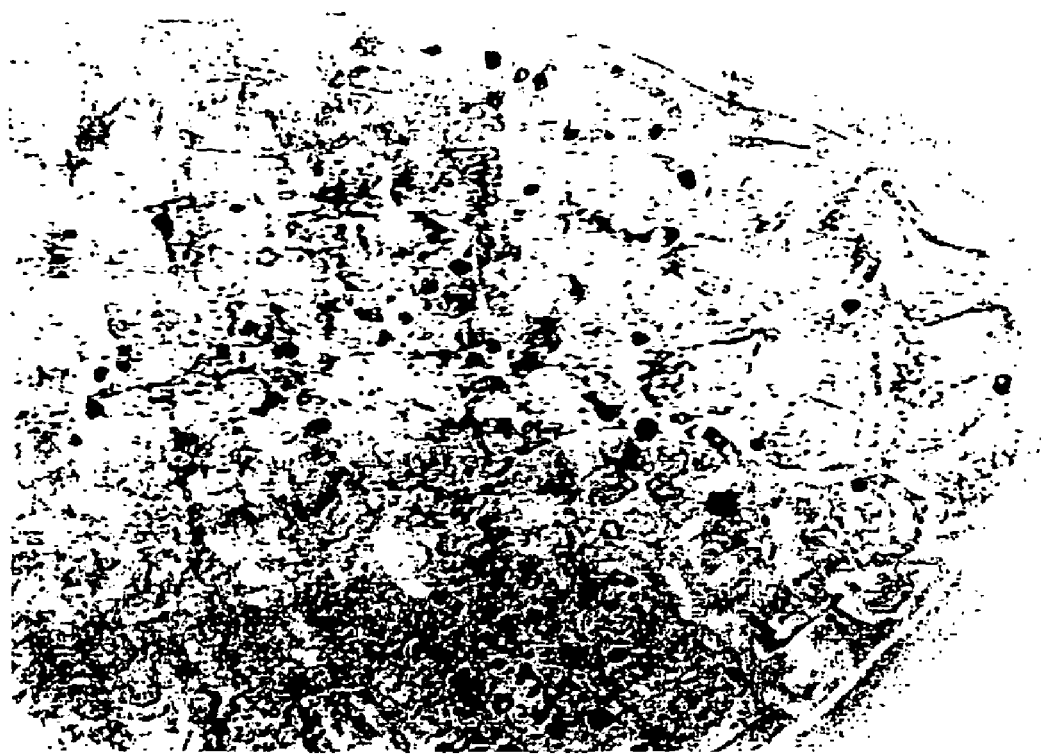
Figure 29:
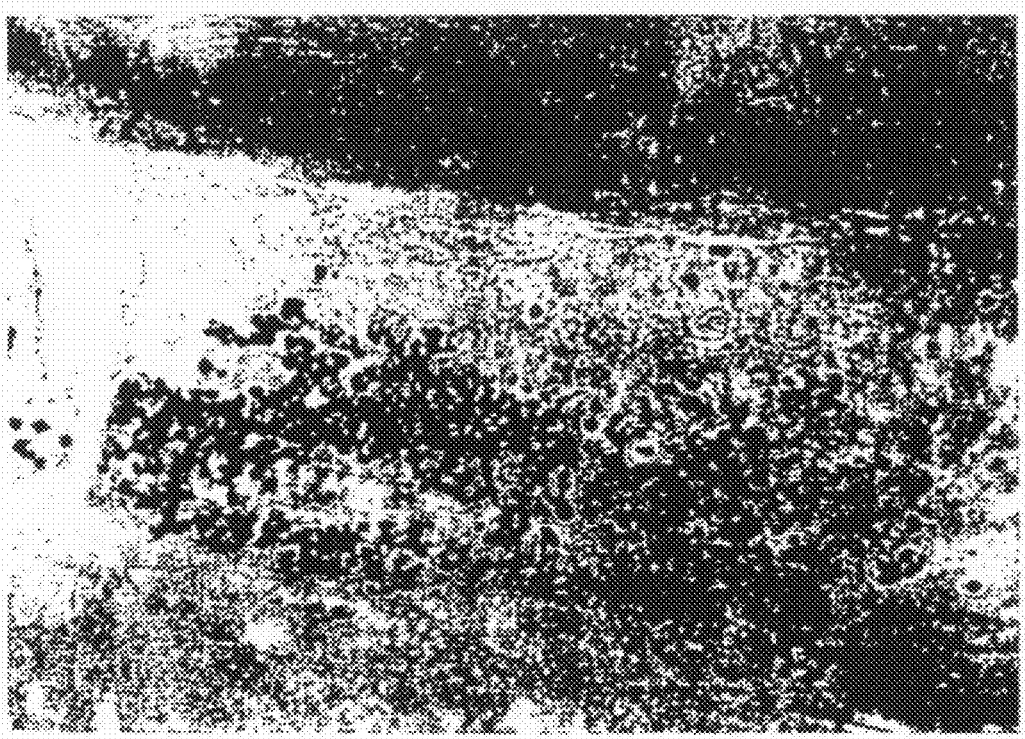
Figure 30:
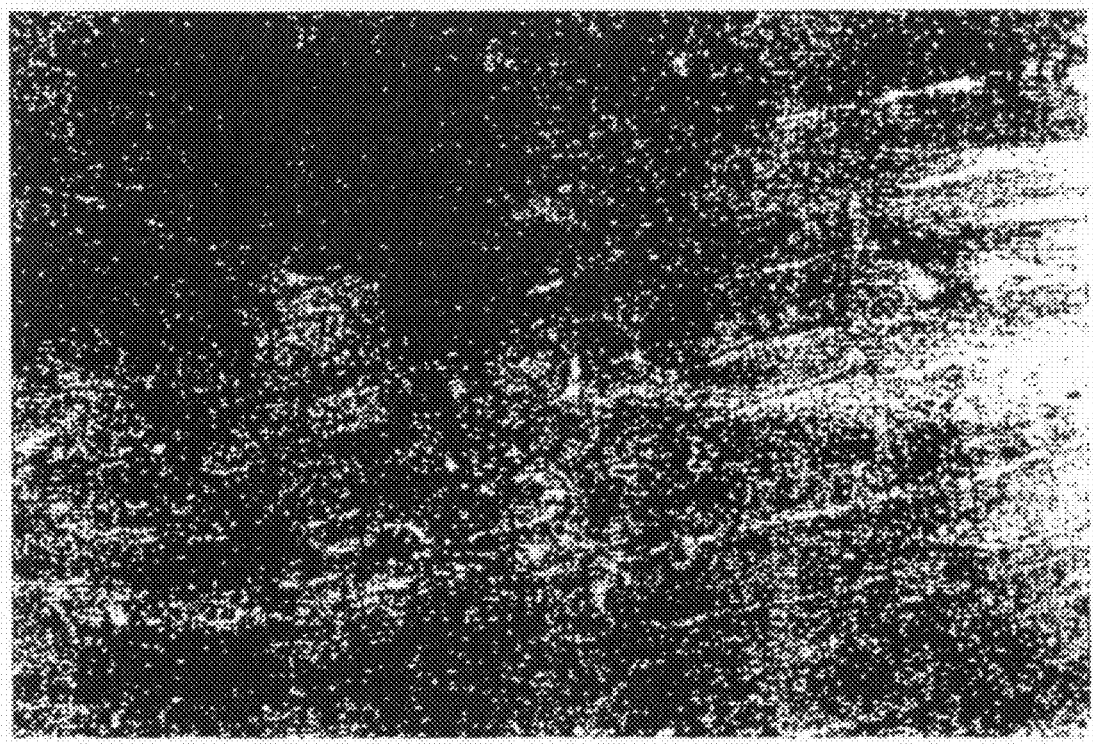

FIG. 28 shows *A. diazotrophicus* UAP5541/pRGH562 (NifH-GUSA) invading the meristem cells of a lateral root of an inoculated plant in accordance with the present invention. Bar=25 µm FIG. 29 shows *A. diazotrophicus* UAP5541/pRGH562 (NifH-GUSA) invading cells of the cortex of a lateral root of an inoculated plant in accordance with the present invention. Bar=5 µm FIG. 30 shows colonies of *A. diazotrophicus* within the vacuole of a living cell of the root cortex of clover inoculated in accordance with the present invention. Bar=25 µm FIG. 31.A shows colonies of *A. diazotrophicus* at high magnification within the vacuole of a living cell of the root cortex of clover. Inoculation was in accordance with the present invention. Bar=5 µm FIG. 31.B shows another region of the root cortex of clover showing numerous colonies of *A. diazotrophicus* within the vacuole of a living cell. Bar=5 µm FIG. 32 shows a large crystal (crystallised from water) of Levan (Sigma L8674). Bar=5 µm

SEED GERMINATION

*Lycopersicon esculentum* var. Ailsa Craig seeds, *Trifolium repens* var. Kent seeds, *Triticum aestivum* var. Hereford seeds, *Brassica napus* var. Express seeds, *Oryza sativa* var. Lemont seeds and *Arabidopsis thaliana* var. Ecotype Col-O seeds were surface sterilised in 15% (v/v) hypochlorite (Domestos) solution for fifteen minutes.

The hypochlorite solution was drained off using a sterile sieve and the seeds were subsequently rinsed six times with sterile deionised water.

The seeds were placed in a sterile 250 ml conical flask containing 15 ml of sterile deionised water. The flask was then placed in a shaker at 24-26° C. in the dark and the seeds left to imbibe for three to four days.

The seeds were then placed on the surface of sterile agar individually in jars (175 ml capacity containing 50 ml of Murashige and Skoog medium (Sigma M5519), 0.8% w/v agar and 3% w/v sucrose) using sterile forceps.

Seedlings were grown for six to seven days under the following conditions:

| Temperature Day | 25° C. |
|---|---|
| Temperature Night | 16° C. |
| Photoperiod | 0600-2200 |

Artificial daylight was provided by 250 $\mu Em^{-2}S^{-1}$ "daylight" fluorescent tubes.

Inoculation with *Acetobacter diazotrophicus*:

Two strains of *Acetobacter diazotrophicus* were used:
*A. diazotrophicus* UAP 5541/p RGS561 (GUS)
*A. diazotrophicus* UAP 5541/p RGH562 (NifH-GUSA)

*Acetobacter diazotrophicus* was streaked onto three 9 cm diameter Petri plates of ATGUS medium containing streptomycin 45 µg/ml and incubated for four to six days at 28° C.

Bacteria were scraped from the plate, using a sterile loop and transferred to sterile 250 ml conical flasks containing 50 ml sterile deionised water. A bacterial suspension was prepared which had an optical density of 0.5-0.6 at a wavelength of 600 nm ($5 \times 10^8$ bacteria/ml). The suspension was diluted $10^{-9}$ (i.e. approx. 1 bacterium/ml).

1 ml of $10^{-9}$ diluted bacterial suspension was added to the base of each plant, after germination of said plant after six to seven days of growth in jars.

To the base of a control plant, 1 ml of sterile deionised water was added.

All plants were grown for a further twelve to twenty days.

Harvesting of Plants for Histochemical Staining:

The plants were removed from the agar. Excess agar was removed by blotting with paper towels. The plants were then histochemically stained for bacterial GUS activity; the GUS gene encodes the enzyme β-glucoronidase, which hydrolyses X-gluc (5-bromo-4-chloro-3-indolyl-β-D-glucoronide cyclohexyl ammonium salt; Gold Biotech, USA) to form an indigo blue coloured compound.

Two controls were set up to ensure that the GUS staining reaction was working, the first using a sample of bacteria taken from the edge of a Murashige and Skoog 8% w/v agar plate and the second was a sample of bacteria grown on ATGUS medium.

Method Used for Staining Bacteria for GUS Activity in Plant Tissues:

Plants previously removed from agar were placed in a vessel such that a minimal amount of staining solution is needed. The staining solution containing X-gluc was added to said vessel, immersing said plants and stored in the dark overnight at 37° C. under vacuum conditions.

The plants were washed three times with 0.1 ml phosphate buffer pH7.0, and fixed with 2% (v/v) glutaraldehyde in 0.1 M phosphate buffer pH7.0 The plants were subsequently viewed for staining by direct light microscopic examination. Plants were dehydrated in an ethanol series and embedded in LR White Resin. Plant sections of 1 µm were prepared for viewing.

Plants inoculated with *Acetobacter diazotrophicus* UAP5541/pRGS561 (constitutively expressing GUS) were assessed for endophytic colonisation 12 to 20 days post inoculation. Histochemically stained plants were examined to detect indigo blue precipitate-stained *Acetobacter diazotrophicus* bacteria by direct microscopic observation of glutaraldehyde fixed plants. For the purposes of this specification histochemically stained bacteria are indicated by black dots.

Figure 1A:
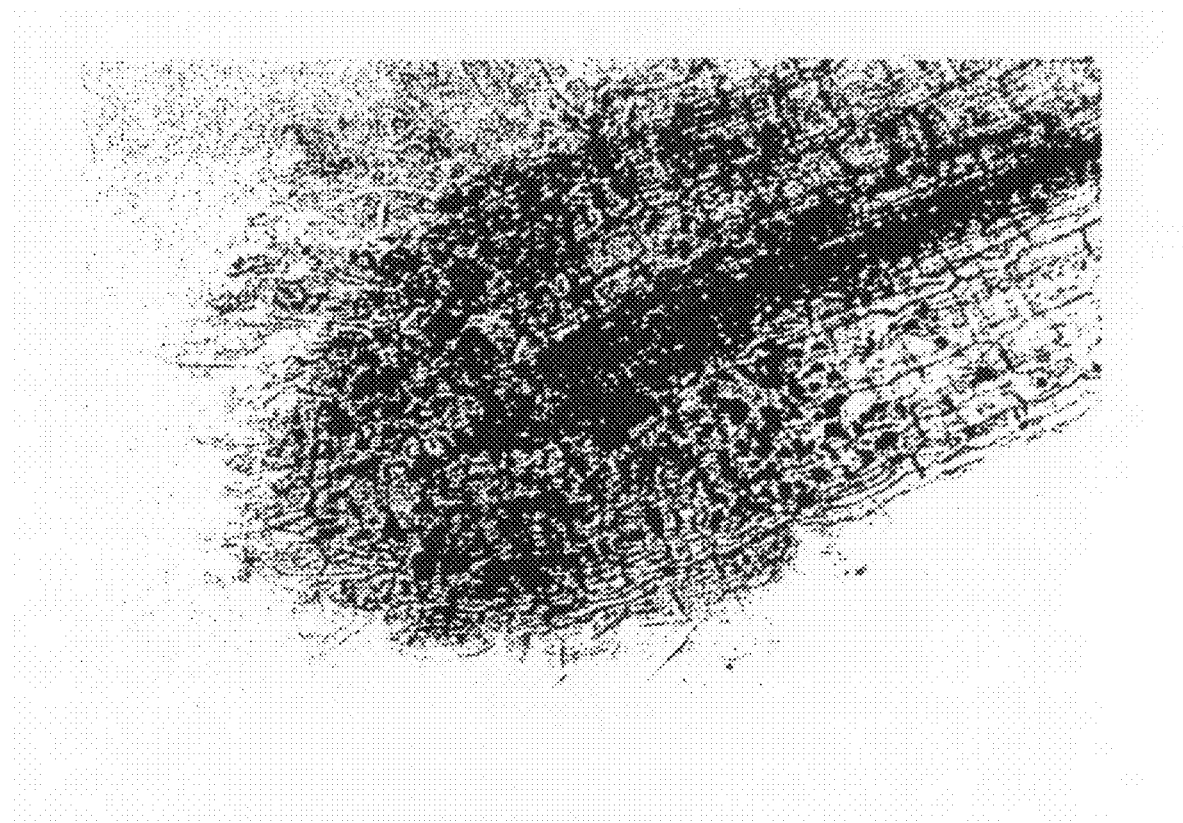
Figure 1B:
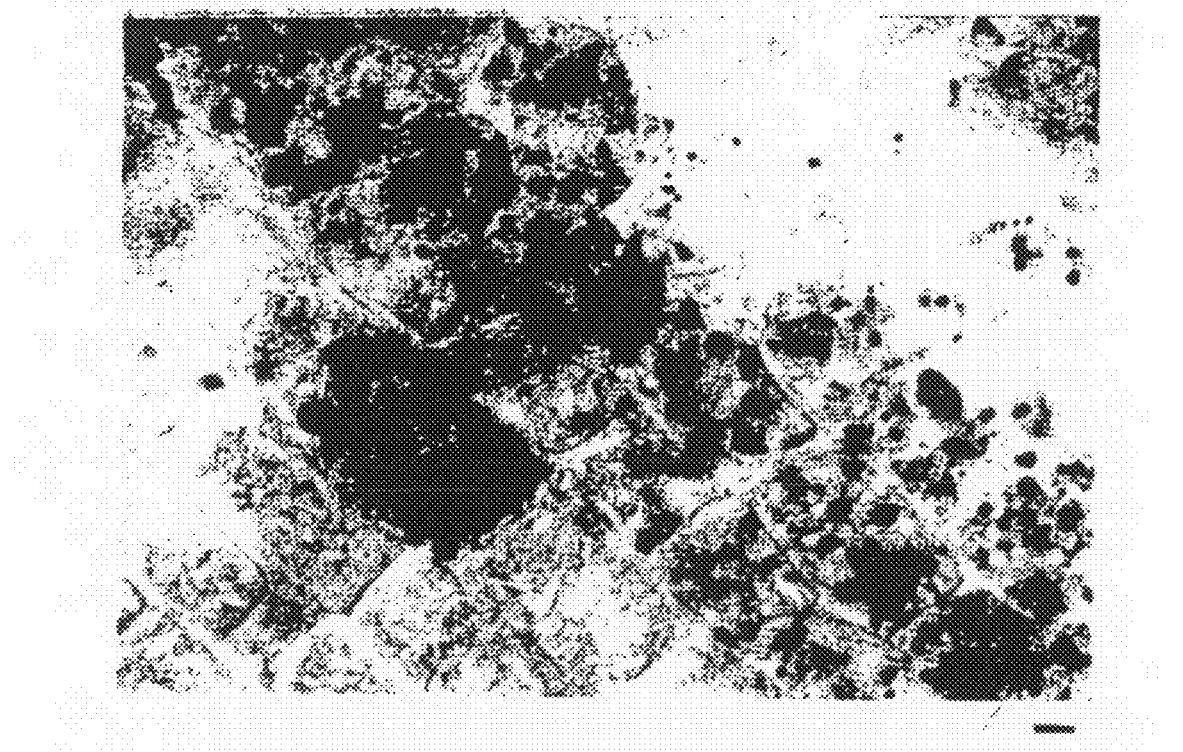
Figure 1C:
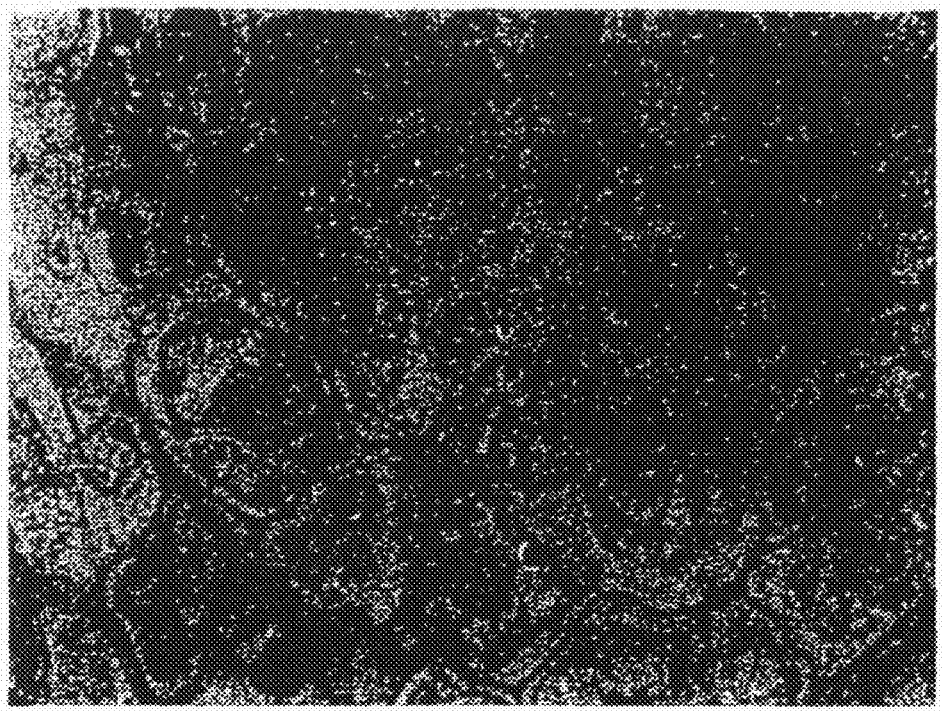
Figure 1D:

It was demonstrated from the results of microscopic analysis that *Acetobacter diazotrophicus* inoculated at an initial concentration of 1 bacterium/ml had invaded the meristematic region of lateral roots via the root tip (FIG. 1A+B) including the meristematic cells and becoming established in vesicles (and then large vacuoles) in the cytoplasm of cells of the meristem, (FIG. 1C+D). The bacteria are indicated as black dots.

Figure 2A:
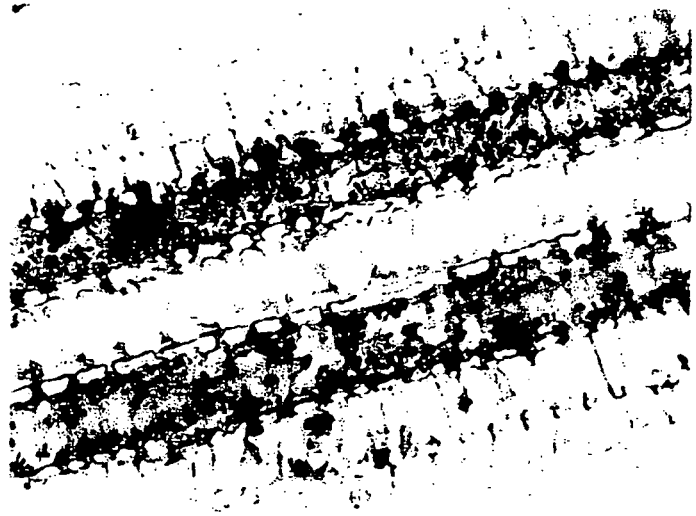
FIG. 2C shows *A. diazotrophicus* UAP5541/pRGS561 GUS in the in the xylem of a primary root in an inoculated plant in accordance with the present invention. Bar=5 µm.
Figure 2B:
Figure 2C:
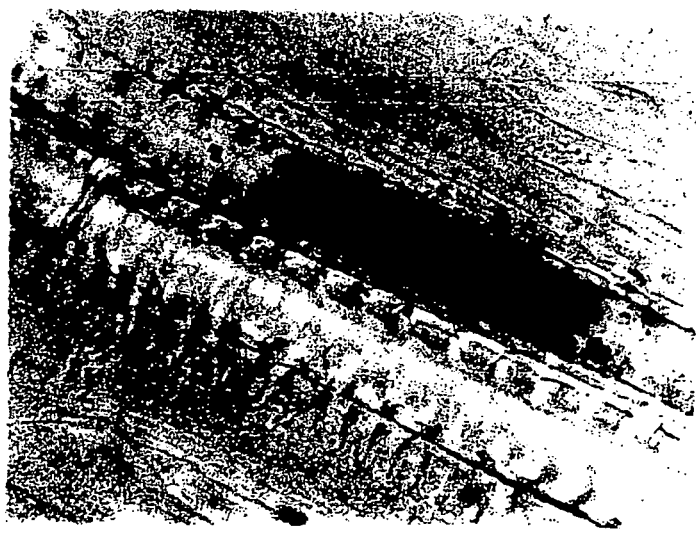

*Acetobacter diazotrophicus* was also seen to have invaded the xylem (FIG. 2A) of the lateral roots forming colonies (indicated by black dots) and also to have invaded cells of the cortex of the root near to the invaded xylem (FIG. 2B). The xylem of primary roots was also invaded by *Acetobacter diazotrophicus* (FIG. 2C).

Figure 3A:
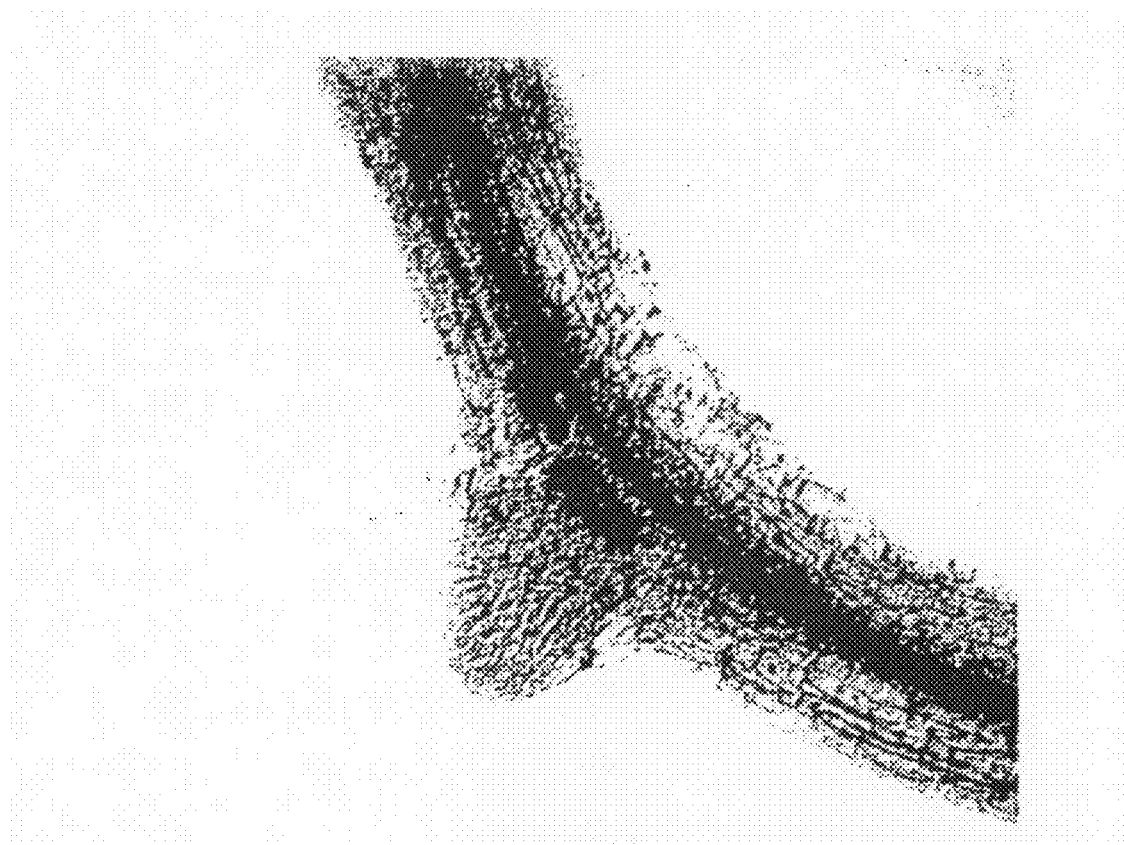
FIG. 3A shows *A. diazotrophicus* UAP5541/pRGS561 GUS invasion of an emerging secondary lateral root of an inoculated plant in accordance with the present invention. Bar=50 µm.
Figure 3B:
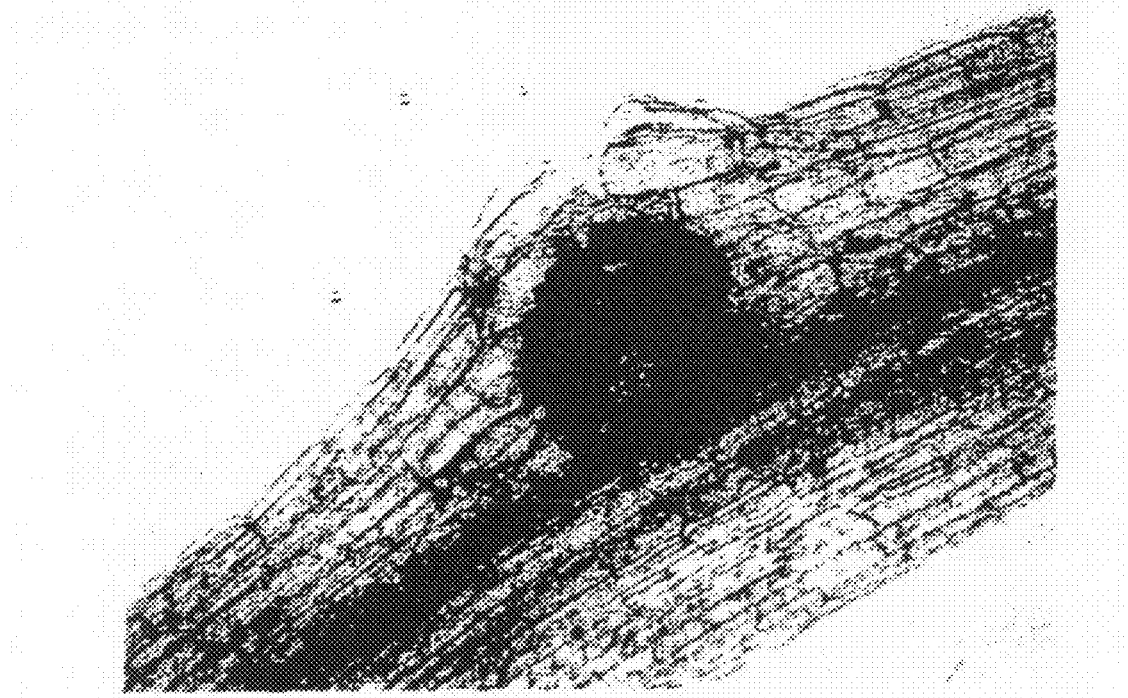
FIG. 3B shows *A. diazotrophicus* UAP5541/pRGS561 GUS invading an emerging secondary lateral root via a crack entry site in an inoculated plant in accordance with the present invention. Bar=25 µm.

Invasion of emerging secondary lateral roots (FIG. 3A) by crack entry (FIG. 3B) in the region of emergence was also observed. Extensive colonisation of cortex cells also occurred (FIGS. 4A and 4B). This is probably by spread of the bacteria (which are highly motile and known to secrete plant cell wall degrading enzymes such as, for example, cellulases and pectinases) from young xylem elements into neighbouring cells, including the phloem (FIG. 4C). FIG. 4D shows a large cortex cell of the root of the plant colonised by *Acetobacter diazotrophicus* (shown as black dots).

Further analysis was carried out on tomato plants inoculated with *Acetobacter diazotrophicus* UAP5541/pRGH562 (NifH-GUSA) in which the expression of the β-glucuronidase gene (GUS) is under the control of a NifH promoter. Consequently, the bacteria will only stain blue in histochemical analysis if nitrogenase genes are being expressed. Staining of *Acetobacter diazotrophicus* UAP5541/pRGH562 (NifH-GUSA) as shown in FIGS. 6 to 13, was comparable to the staining of constitutively expressed GUS in *Acetobacter diazotrophicus* UAP5541/pRGS561 GUS (FIGS. 1 to 5). The bacteria in these figures are indicated by black dots.

FIG. 6 shows a plant root tip inoculated at an initial concentration of 1 bacterium/ml. Bacteria can be seen as a black stain in the root tip. Bacteria also invaded emerging lateral roots (FIG. 7). FIG. 8A shows bacteria colonising meristem cells of a root and FIG. 8B is an oil immersion picture showing black stained bacteria inside cells of the meristem. FIG. 9 shows, using an oil immersion objective lens, cells from a root cortex of the plant. The bacteria (shown in black) are seen inside cells of the root cortex. It is interesting to note that the bacteria form uniform rhomboidal shaped colonies. These colonies are packages of bacteria probably embedded in the colourless oligofructoside polymer, levan. *Acetobacter diazotrophicus* is known to produce levan which could act to promote aggregation of bacteria into these crystalline-like clusters and provide thereby oxygen protection of their nitrogenase. FIG. 10 shows the bacteria in the vascular system of the root and FIG. 11 shows bacteria in the xylem and cells of the root cortex. The bacteria were also found in the vascular system of the stem as shown in FIG. 12 which also shows the spread of bacteria from the xylem to the phloem region in the plant stem.

*Acetobacter diazotrophicus* was also seen in chloroplast containing cells (FIG. 13) in the stem of the plant.

FIGS. 14 to 19 show analysis on the legume clover plants inoculated with *Acetobacter diazotrophicus* UAP5541/pRGH562 (NifH-GUSA) in which the expression of the β-glucoronidase gene (GUS) is under the control of a NifH promoter. Consequently, the bacteria will only stain blue in histochemical analysis if nitrogenase genes are being expressed. Intracellular invasion of living cells, systemic colonisation of the plant and staining of *Acetobacter diazotrophicus* UAP5541/pRGH562 (NifH-GUSA) as shown in FIGS. 14 to 19 was comparable to that shown in the non-legume, tomato plants, FIG. 6 to FIG. 13, similarly inoculated with *Acetobacter diazotrophicus* UAP5541/pRGH562 (NifH-GUSA) at an initial concentration of 1 bacterium/ml. Systemic invasion of the leaves was very evident (FIG. 16 to FIG. 19). The bacteria in the above figures are indicated by black dots.

FIGS. 20, 21 and 22 show analysis of cereal wheat plants inoculated with *Acetobacter diazotrophicus* UAP5541/pRGH562 (NifH-GUSA) in which the expression of the β-glucuronidase gene (GUS) is under the control of a NifH promoter. Consequently, the bacteria will only stain blue in the histochemical analysis if nitrogenase genes are being expressed. Intracellular invasion of living cells, systemic colonisation of plant and staining of *Acetobacter diazotrophicus* UAP5541/pRGH562 (NifH-GUSA) as shown on FIGS. 20 to 22 was comparable to that shown in non-legume tomato (FIGS. 6 to 13) and legume clover plants (FIGS. 14 to 19) similarly inoculated with *Acetobacter diazotrophicus* UAP5541/pRGH562 (NifH-GUSA) at an initial concentration of 1 bacterium/ml. Systemic invasion of the epidermal cells of the leaves was very evident (FIG. 22). The bacteria in the above figures are indicated by black dots.

FIGS. 23, 24 and 25 show analysis on oilseed rape plants similarly inoculated with *Acetobacter diazotrophicus* UAP5541/pRGH562 (NifH-GUSA). Intracellular invasion of living cells, systemic colonization of the plant and the staining of *Acetobacter diazotrophicus* UAP5541/pRGH562 (NifH-GUSA) was comparable to that observed in tomato, clover and wheat similarly inoculated.

FIGS. 26 and 27 show analysis of the cerial rice (*Oryza sativa*) similarly inoculated with *Acetobacter diazotrophicus* UAP 5541/pRGH 562 (NifH-GUSA). Intracellular invasion of living cells, systemic colonisation of the plant and the staining of *Acetobacter* diazotrophicus UAP 5541/pRGH 562 (Nif H-GUSA) was comparable to that observed in tomato, clover, wheat and oilseed rape plants similarly inoculated.

FIGS. 28 and 29 show analysis of the model plant *Arabidopsis thaliana* inoculated with *Acetobacter diazotrophicus* UAP 5541/pRGH562 (Nif H-GUSA) in accordance with the present invention. Intracellular invasion of living cell, systemic colonisation of the plant and the staining of *Acetobacter diazotrophicus* UAP 5541/pRGH562 (Nif H-GUSA) was comparable to that observed in tomato, clover, wheat, oilseed rape and cereal rice plants similarly inoculated.

Method Used for Staining with Neutral Red

Neutral Red (Merck index No. 6571) is a biological stain which is non-toxic. Plant cells are still viable after staining with 0.01% W/V Neutral Red in water. Plants inoculated with *Acetobacter diazotrophicus* in accordance with the present invention were placed in a solution of neutral red (0.9% W/V in water) for 30 minutes. The plants were then washed and prepared for microscopic examination.

Figure 31A:
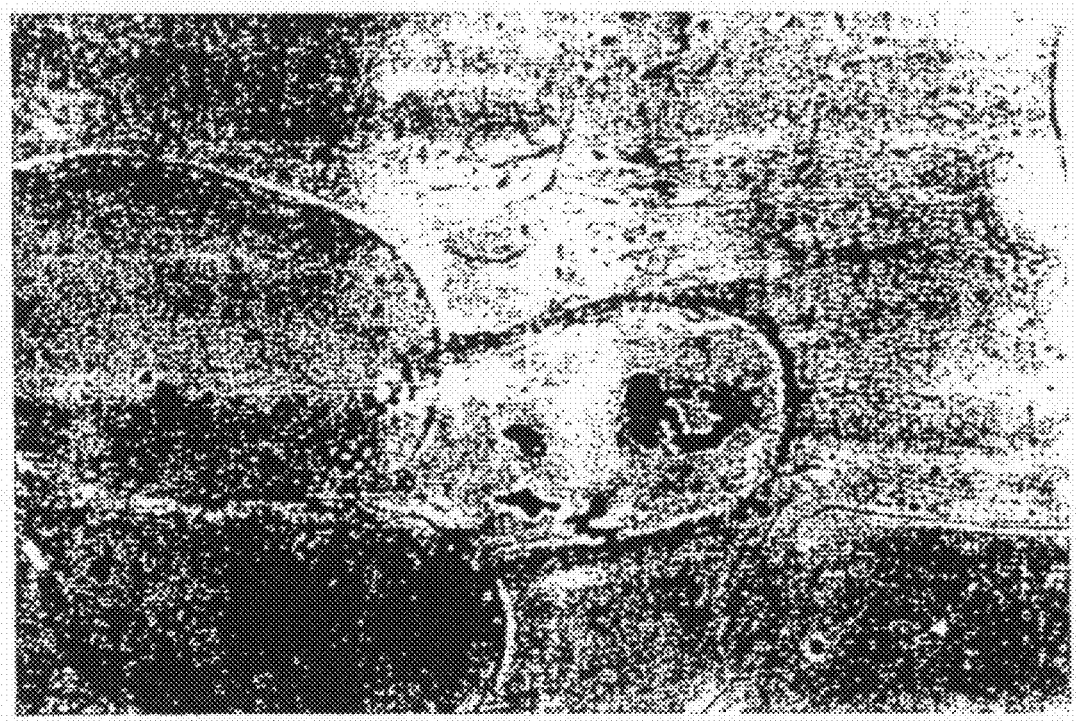
Figure 31B:
Figure 32:
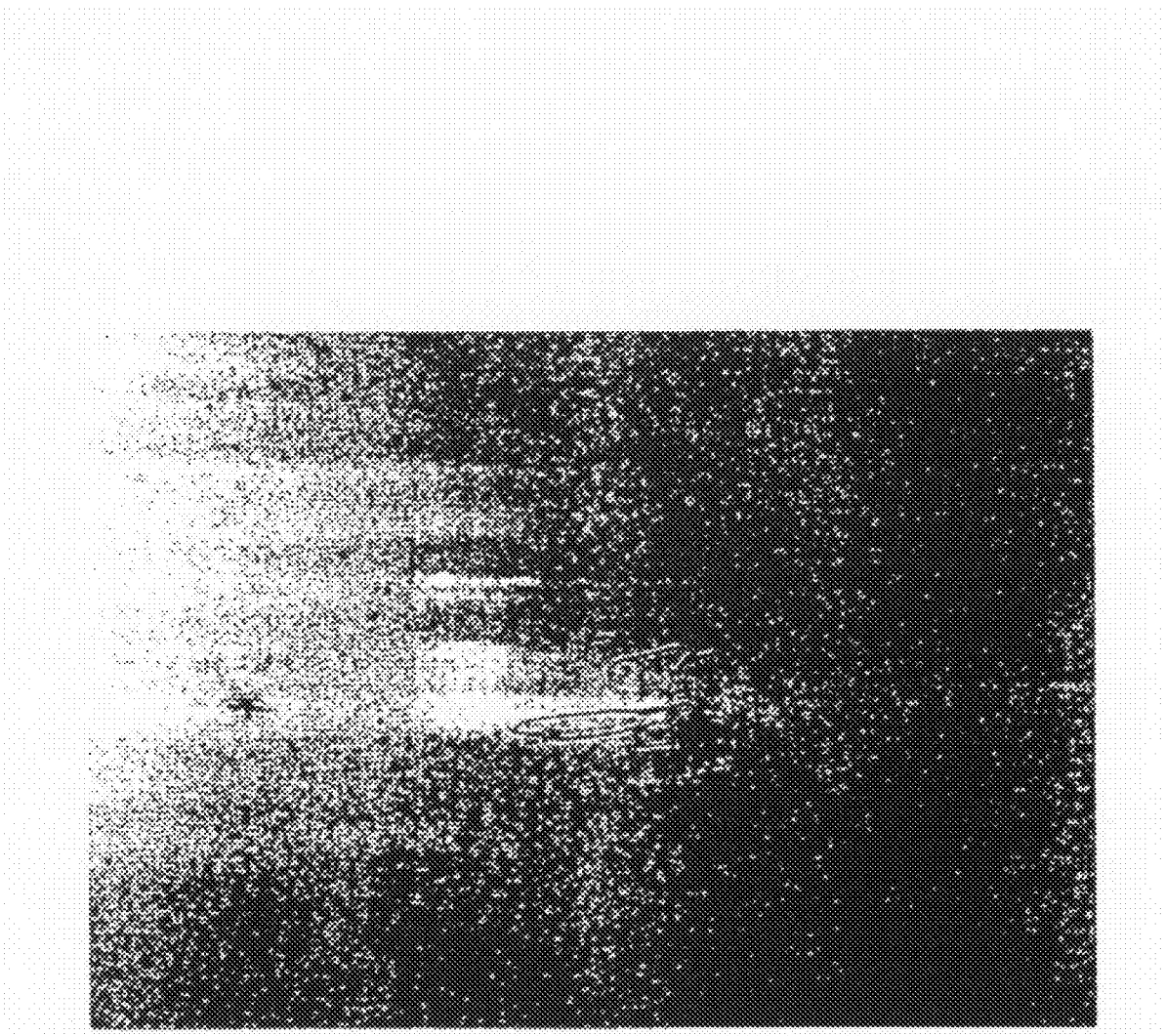

FIG. 30, 31A and 31B show analysis of *Acetobacter diazotrophicus* in living cells of clover. This analysis was performed to ensure that the *Acetobacter diazotrophicus* bacteria inoculated into clover in accordance with the present invention were actually present intracellularly in living cells. Neutral red was used for this purpose. At low pH (a pH less than 7.0) cellular compartments that are acidic stain red. At higher pH (a pH above 7.0) neutral red is presented as a yellow stain. FIGS. 30 and 31A show colonies (black dots) of *Acetobacter diazotrophicus* within a vacuole of a living cell of the root cortex of clover inoculated in accordance with the present invention. FIG. 31B shows another region of the root cortex of clover with *Acetobacter diazotrophicus* (black dots) present in the vacuole of a living cell.

*Acetobacter diazotrophicus* is present in living cells as polyhedral colonies. These polyhedral structures are caused by the secretion of a polymer of β-D-fructose called Levan. Crystals of Levan isolated from *Erwinia herbicola* (sigma cat. No. L8647) closely resemble the shape of colonies of *Acetobacter diazotrophicus* found in plants inoculated in accordance with the present invention (FIG. 32).

Wheat (*Triticum aestivum*) and clover (*Trifolium repens*), innoculated with *A. diazotrophicus* UAP 5541/pRGH562 (Nif H-GUSA) in accordance with the present invention, were transferred after two weeks inoculation in jars (75 ml capacity containing 50 ml of Murashige and Skoog medium, 0.8% W/V agar and 3% W/V sucrose), to (seed and cutting) compost in pots for four weeks. The plants in pots were incubated under clean growth room conditions (25° C. day temperature, 16° C. night temperature, photoperiod of 250 $\mu Em^{-2}S^{-1}$ from 'Daylight' fluorescent tubes, 0600-2200) and watered with sterile water. Plants were assayed for nitrogenase activity using the acetylene reduction assay. Uninoculated controls were also similarly transferred from jars to compost and assayed for nitrogenase activity using the acetylene reduction assay.

Acetylene Reduction Assay

Nitrogenase, the enzyme responsible for the reduction of gaseous nitrogen (N≡N) to ammonia ($NH_3$) (nitrogen fixation), was assayed by gas chromatography. In this assay, plants are incubated with excess acetylene gas (H—C≡CH) which is reduced by nitrogenase acting on the triple bond of acetylene to yield ethylene (H2—C═C—$H_2$). Plants were rinsed in sterile water and transferred to 75 ml Pyrex tubes which were then capped with gas tight Subaseals™. 10% of the air volume was removed using a hypodermic syringe, and replaced with acetylene. The samples were returned to the growth room and incubated for 24 hours under the same conditions used for the growth of plants inoculated with *A. diazotrophicus* (25° C., day temperature, 16° C., night temperature, photoperiod of 250 $\mu Em^{-2}S^{-1}$ from "Daylight" fluorescent tubes, 0600-2200). Samples of gases (0.5 ml) were removed in syringes and analysed for ethylene production with a Pye Unicam PU 4500 gas chromatograph with 183 cm (2.0 mm internal diameter) glass column containing 'Propack N' with a mesh size of 80-100. The mobile phase carrier was $N_2$ at a flow rate of 27 ml $min^{-1}$. The oven containing the column was set at 60° C. and the flame detector set to 121° C. The instrument was calibrated (peak height: ethylene (number of nanomoles) per 0.5 ml sample) using a standard curve.

| Inoculated | Uninoculated (control) |
|---|---|
| WHEAT (nanomoles ethylene per 24 hours) | |
| 31* | 7 |
| 12* | 6 |
| 6 | 7 |
| 6 | 7 |
| 15* | 6 |

*Nitrogenase activity of individual wheat plant (-control) 24, 6 & 9 nanomoles ethylene respectively.

| Inoculated | Uninoculated (control) |
|---|---|
| CLOVER (nanomoles ethylene per 24 hours) | |
| 4 | 6 |
| 6 | 7 |
| 5 | 5 |
| 3 | 3 |
| 5 | 6 |
| 15* | 3 |

*Nitrogenase activity of individual clover plant (-control): 12, nanomoles ethylene.

When clover was inoculated with *Rhizobium leguminosarum* biovar *Trifolii* (RCR5), under these growth conditions, nodulated plants were produced and these had a mean nitrogenase activity per clover plant of 60 nanomoles ethylene per 24 hours.

The invention claimed is:

1. A non-leguminous or leguminous plant containing nitrogen fixing bacteria, *Acetobacter diazotrophicus* (syn. *Gluconacebobacter diazotrophicus*), said bacteria being located intracellularly in living plant cells of said plant and providing fixed nitrogen to said plant wherein said nitrogen fixing bacteria are present in membrane bound vescicles and vacuoles within the cytoplasm of the living plant cells.

2. A plant according to claim 1 obtained by a method of inoculating said plant with between 1 and 100 of said bacteria per millilitre of inoculum.

3. A plant according to claim 1 obtained by a method of inoculating said plant with between 1 and 10 of said bacteria per millilitre of inoculum.

4. A plant according claim 1 wherein the bacteria spread from plant cell to plant cell by division of plant cells in the meristem and subsequent divisions thereof.

5. A plant according to claim 1 wherein the bacteria become systemic by moving through the xylem.

6. A plant according to claim 1 wherein the bacteria become systemic by divisions of plant cells and subsequent divisions thereof.

7. A method of producing a leguminous or non-leguminous plant in accordance with claim 1, wherein said bacteria are introduced by inoculation of said plant with between 1 and 100 bacteria per millilitre of inoculum when germination of said plant occurs or up to seven days thereafter, and wherein said bacteria become systemic by division of plant cells and subsequent divisions thereof.

8. A method of inoculating a non-leguminous or a leguminous plant with nitrogen fixing bacteria, *Acetobacter diazotrophicus* (syn. *Gluconacetobacter diazotorphicus* to produce a plant in accordance with claim 1 which comprises inoculating said plant with between 1 and 100 of said bacteria per millilitre of inoculum when germination of said plant occurs or up to seven days thereafter.

9. A method according to claim 8 wherein the non-leguminous or leguminous plant is inoculated with 1-10 bacteria per millilitre of inoculum.

* * * * *